US008126734B2

(12) United States Patent
Dicks et al.

(10) Patent No.: US 8,126,734 B2
(45) Date of Patent: *Feb. 28, 2012

(54) SYSTEMS AND METHODS FOR ADAPTER-BASED COMMUNICATION WITH A MEDICAL DEVICE

(75) Inventors: Kent Dicks, Scottsdale, AZ (US); Ralph Kent, Scottsdale, AZ (US); Robert Tripp, Fountain Hills, AZ (US); Terry Bartlett, Cave Creek, AZ (US); Thomas Crosley, Gilbert, AZ (US)

(73) Assignee: MedApps, Inc., Scottsdale, AZ (US)

( * ) Notice: Subject to any disclaimer, the term of this patent is extended or adjusted under 35 U.S.C. 154(b) by 417 days.

This patent is subject to a terminal disclaimer.

(21) Appl. No.: 11/876,744

(22) Filed: Oct. 22, 2007

(65) Prior Publication Data
US 2008/0097911 A1   Apr. 24, 2008

Related U.S. Application Data

(60) Provisional application No. 60/862,743, filed on Oct. 24, 2006.

(51) Int. Cl.
G06F 3/00   (2006.01)
G06Q 50/00   (2006.01)
A61B 5/00   (2006.01)

(52) U.S. Cl. .................... 705/2; 705/3; 710/15; 710/16; 600/300

(58) Field of Classification Search .................. 705/2–3; 710/15–16; 600/300
See application file for complete search history.

(56) References Cited

U.S. PATENT DOCUMENTS

| 5,006,699 A | 4/1991 | Felkner et al. |
| 5,673,692 A | 10/1997 | Schulze et al. |
| 5,721,780 A | 2/1998 | Ensor et al. |

(Continued)

FOREIGN PATENT DOCUMENTS
AU   2002100889   6/2003
(Continued)

OTHER PUBLICATIONS

Blount et al., "Remote health-care monitoring using Personal Care Connect", IBM Systems Journal, vol. 46, No. 1, pp. 95-113, (2007).

(Continued)

*Primary Examiner* — Lena Najarian
*Assistant Examiner* — Minnah Seoh
(74) *Attorney, Agent, or Firm* — Snell & Wilmer LLP

(57) ABSTRACT

A system according to one aspect of the present invention comprises a processor, a device interface, a data relay transceiver, and a memory coupled to the processor and storing instructions. The processor executes the instructions in the memory to receive data from a medical device through a wired connection using the device interface, where the data is received through an adapter coupled to the device interface and that communicates with the medical data interchange device using a first communication format and with the medical device using a second communication format. The processor further executes the instructions in the memory to transmit the data to an intermediary device using the data relay transceiver. This system can be implemented in a small, portable unit that is easy for a patient to transport. The adapter can be removably coupled to the medical data interchange device to allow different adapters configured to communicate with different medical devices to be used with a single medical data interchange device.

25 Claims, 15 Drawing Sheets

U.S. PATENT DOCUMENTS

| | | |
|---|---|---|
| 5,724,985 A | 3/1998 | Snell et al. |
| 5,772,586 A | 6/1998 | Heinonen et al. |
| 5,891,180 A | 4/1999 | Greeninger et al. |
| 5,936,523 A | 8/1999 | West |
| 6,024,699 A | 2/2000 | Surwit et al. |
| 6,034,963 A | 3/2000 | Minami et al. |
| 6,093,146 A | 7/2000 | Filangeri |
| 6,302,844 B1 | 10/2001 | Walker et al. |
| 6,336,900 B1 | 1/2002 | Alleckson et al. |
| 6,402,691 B1 | 6/2002 | Peddicord et al. |
| 6,416,471 B1 | 7/2002 | Kumar et al. |
| 6,443,890 B1 | 9/2002 | Schulze et al. |
| 6,443,891 B1 | 9/2002 | Grevious |
| 6,478,736 B1 | 11/2002 | Mault |
| 6,485,418 B2 | 11/2002 | Yasushi et al. |
| 6,579,231 B1 | 6/2003 | Phipps |
| 6,580,948 B2 | 6/2003 | Haupert |
| 6,598,084 B1 | 7/2003 | Edwards et al. |
| 6,625,642 B1 | 9/2003 | Naylor et al. |
| 6,790,178 B1 | 9/2004 | Mault et al. |
| 6,804,558 B2 | 10/2004 | Haller et al. |
| 6,807,965 B1 | 10/2004 | Hickle |
| 6,893,396 B2 | 5/2005 | Schulze et al. |
| 6,903,657 B2 | 6/2005 | Kwoen |
| 6,915,267 B2 | 7/2005 | Jackson et al. |
| 6,957,107 B2 | 10/2005 | Rogers et al. |
| 6,978,182 B2 | 12/2005 | Mazar et al. |
| 7,039,810 B1 | 5/2006 | Nichols |
| 7,044,911 B2 | 5/2006 | Drinan et al. |
| 7,129,836 B2 | 10/2006 | Lawson et al. |
| 7,134,996 B2 | 11/2006 | Bardy |
| 7,154,398 B2 | 12/2006 | Chen et al. |
| 7,156,808 B2 | 1/2007 | Quy |
| 7,161,484 B2 | 1/2007 | Tsoukalis |
| 7,181,017 B1 | 2/2007 | Nagel et al. |
| 7,231,258 B2 | 6/2007 | Moore et al. |
| 7,242,306 B2 | 7/2007 | Wildman et al. |
| 7,265,676 B2 | 9/2007 | Gordon et al. |
| 7,311,666 B2 | 12/2007 | Stupp et al. |
| 7,438,216 B2 | 10/2008 | Ambekar |
| 7,590,191 B1 | 9/2009 | Macrae |
| 7,733,224 B2 | 6/2010 | Tran |
| 7,761,261 B2 | 7/2010 | Shmueli et al. |
| 2001/0005772 A1 | 6/2001 | Kisakibaru |
| 2001/0051787 A1 | 12/2001 | Haller et al. |
| 2002/0029157 A1 | 3/2002 | Marchosky |
| 2002/0072933 A1 | 6/2002 | Vonk et al. |
| 2002/0128804 A1 | 9/2002 | Geva |
| 2003/0009088 A1 | 1/2003 | Korth et al. |
| 2003/0018742 A1 | 1/2003 | Imago |
| 2003/0050539 A1 | 3/2003 | Naghavi et al. |
| 2003/0072424 A1 | 4/2003 | Evans |
| 2003/0088295 A1 | 5/2003 | Cox |
| 2003/0088441 A1 | 5/2003 | McNerney |
| 2003/0095675 A1 | 5/2003 | Marlow et al. |
| 2003/0149593 A1 | 8/2003 | Mok et al. |
| 2003/0216625 A1 | 11/2003 | Phipps |
| 2004/0015132 A1 | 1/2004 | Brown |
| 2004/0078220 A1 | 4/2004 | Jackson |
| 2004/0097796 A1 | 5/2004 | Berman et al. |
| 2004/0100376 A1 | 5/2004 | Lye et al. |
| 2004/0102683 A1 | 5/2004 | Khanuja et al. |
| 2004/0122488 A1* | 6/2004 | Mazar et al. ............ 607/60 |
| 2004/0127775 A1 | 7/2004 | Miyazaki et al. |
| 2004/0152961 A1 | 8/2004 | Carlson et al. |
| 2004/0199056 A1 | 10/2004 | Husemann et al. |
| 2004/0210458 A1 | 10/2004 | Evans |
| 2005/0002341 A1 | 1/2005 | Lee et al. |
| 2005/0004700 A1 | 1/2005 | DiMaggio |
| 2005/0021370 A1 | 1/2005 | Riff et al. |
| 2005/0038680 A1 | 2/2005 | McMahon |
| 2005/0060187 A1 | 3/2005 | Gottesman |
| 2005/0065815 A1 | 3/2005 | Mazar et al. |
| 2005/0070767 A1 | 3/2005 | Maschke |
| 2005/0119580 A1 | 6/2005 | Eveland |
| 2005/0137465 A1 | 6/2005 | Cuddihy et al. |
| 2005/0149358 A1 | 7/2005 | Sacco |
| 2005/0171410 A1 | 8/2005 | Hjelt et al. |
| 2005/0171762 A1 | 8/2005 | Ryan et al. |
| 2005/0192649 A1 | 9/2005 | Shehadeh et al. |
| 2005/0197545 A1 | 9/2005 | Hoggle |
| 2005/0203775 A1 | 9/2005 | Chesbrough |
| 2005/0234307 A1 | 10/2005 | Heinonen et al. |
| 2005/0240111 A1 | 10/2005 | Chung |
| 2006/0020302 A1 | 1/2006 | Torgerson et al. |
| 2006/0026118 A1 | 2/2006 | Jung et al. |
| 2006/0035669 A1 | 2/2006 | Chuprun et al. |
| 2006/0036134 A1 | 2/2006 | Tarassenko et al. |
| 2006/0063980 A1 | 3/2006 | Hwang et al. |
| 2006/0064320 A1 | 3/2006 | Postrel |
| 2006/0089542 A1 | 4/2006 | Sands |
| 2006/0111079 A1 | 5/2006 | Tischer et al. |
| 2006/0116744 A1 | 6/2006 | Von Arx et al. |
| 2006/0135858 A1 | 6/2006 | Nidd et al. |
| 2006/0142648 A1 | 6/2006 | Banet et al. |
| 2006/0161222 A1 | 7/2006 | Haubrich et al. |
| 2006/0167346 A1 | 7/2006 | Sarel |
| 2006/0200007 A1 | 9/2006 | Brockway et al. |
| 2006/0202816 A1 | 9/2006 | Crump et al. |
| 2006/0205564 A1 | 9/2006 | Peterson |
| 2006/0212316 A1 | 9/2006 | Jackson et al. |
| 2006/0218011 A1 | 9/2006 | Walker et al. |
| 2006/0235280 A1 | 10/2006 | Vonk et al. |
| 2006/0242295 A1 | 10/2006 | Husemann et al. |
| 2006/0253301 A1 | 11/2006 | Simms et al. |
| 2006/0270421 A1 | 11/2006 | Phillips et al. |
| 2006/0293607 A1 | 12/2006 | Alt et al. |
| 2007/0002791 A1 | 1/2007 | Kasprzyk et al. |
| 2007/0004969 A1 | 1/2007 | Kong et al. |
| 2007/0015974 A1 | 1/2007 | Higgins et al. |
| 2007/0016450 A1 | 1/2007 | Bhora et al. |
| 2007/0033072 A1 | 2/2007 | Bildirici |
| 2007/0055552 A1 | 3/2007 | St. Clair et al. |
| 2007/0061167 A1 | 3/2007 | Brown |
| 2007/0073266 A1 | 3/2007 | Chmiel et al. |
| 2007/0078497 A1 | 4/2007 | Vandanacker |
| 2007/0083246 A1 | 4/2007 | Mazar et al. |
| 2007/0135855 A1 | 6/2007 | Foshee et al. |
| 2007/0143398 A1 | 6/2007 | Graham |
| 2007/0188323 A1 | 8/2007 | Sinclair et al. |
| 2007/0239229 A1 | 10/2007 | Masoud et al. |
| 2007/0250130 A1 | 10/2007 | Ball et al. |
| 2007/0253380 A1 | 11/2007 | Jollota et al. |
| 2007/0267475 A1 | 11/2007 | Hoglund et al. |
| 2008/0059239 A1 | 3/2008 | Gerst et al. |
| 2008/0065412 A1 | 3/2008 | Vallone |
| 2008/0126131 A1 | 5/2008 | Lou |
| 2009/0048865 A1 | 2/2009 | Breazeale, Jr. |
| 2009/0204434 A1 | 8/2009 | Breazeale, Jr. |
| 2011/0093287 A1 | 4/2011 | Dicks et al. |

FOREIGN PATENT DOCUMENTS

| | | |
|---|---|---|
| WO | 00/49549 | 8/2000 |
| WO | WO 02/058307 | 7/2002 |
| WO | 2005079667 | 9/2005 |
| WO | 2005/101279 | 10/2005 |
| WO | 2006/006159 | 1/2006 |
| WO | 2006060669 | 6/2006 |

OTHER PUBLICATIONS

Milenkovic et al., "Wireless sensor networks for personal health monitoring: Issues and an implementation", Computer Communications, 13 pages (2006).

Michael Setton et al., "Bluetooth sensors for wireless home and hospital healthcare monitoring", Cyberfab, 6 pages, date unknown.

Korhonen et al., "Health Monitoring in the Home of the Future", IEEE Engineering in Medicine and Biology Magazine, pp. 66-73 (May/Jun. 2003).

"WHMS—Wearable Health Monitoring Systems", Electrical and Computer Engineering, The University of Alabama in Huntsville, http://www.ece.uah.edu/~jovanov/whrms/, 13 pages.

Hung et al., "Implementation of a WAP-Based Telemedicine System for Patient Monitoring", IEEE Transactions of Information Technology in Biomedicine, vol. 7, No. 2, pp. 101-107 (Jun. 2003).

Lee et al., "Design and Implementation of a Mobile-Care System over Wireless Sensor Network for Home Healthcare Applications", Proceedings of the 28th IEEE EMBS Annual International Conference, pp. 6004-6007 (Aug./Sep. 2006).
Chen et al., "An i-Mode Portable Healthcare Monitor", Proceedings of the Second Joint EMBS/BMES Conference, IEEE, pp. 1851-1852 (2002).
Kuo et al., "Design and Implementation of Internet-Based In-House Healthcare and Home Automation Systems", IEEE, pp. 2944-2949 (2003).
Jovanov et al., "Stress Monitoring Using a Distributed Wireless Intelligent Sensor System", IEEE Engineering in Medicine and Biology Magazine, pp. 49-55 (May/Jun. 2003).
Lubrin et al., "Wireless Remote Healthcare Monitoring with Motes", Proceedings of the International Conference on mobile Business, IEEE Computer Society, 7 pages (2005).
Guo et al , "Implementing a wireless portable healthcare monitoring system for physiological signals", The Institute of Engineering and Technology, 1 page (2007).
Otto et al., "System Architecture of a Wireless Body Area Sensor Network for Ubiquitous Health Monitoring", Journal of Mobile Multimedia, vol. 1, No. 4., pp. 307-326 (2006).
Yu et al., "A Wireless Physiological Signal Monitoring System with Integrated Bluetooth and WiFi Technologies", Proceedings of the 2005 IEEE Engineering in Medicine and Biology 27th Annual Conference, pp. 2203-2206 (2005).
"Body Area Networks—A "Healthy Aims" Projects", Zarlink Semiconductor Inc., 1 page (2007).
"Bionformatics" downloaded from webpage http://en.wikipedia.org/wiki/Bioinformatics on Aug. 2, 2007 (9 pages).
Mintz, "Microsoft Launches Health Records Site," downloaded from webpage http://bz.yahoo.com/ap/071004/microsoft_healthvault.html?.v=1 on Dec. 18, 2007 (3 pages).
"Bluetooth Sig Aims to Improve Healthcare Experience Through Interoperability," downloaded from webpage http://www.bluetooth.com/Bluetooth/Press/SIG/BLUETOOTH_SIG_AIMS_TO_IMPROVE_HEALTHCARE_EXPERIENCE_THROUGH_INTEROPERABILITY.htm (2 pages).
USPTO; Advisory Action dated May 10, 2011 in U.S. Appl. No. 11/876,708.
USPTO; Final Office Action dated Jun. 22, 2011 in U.S. Appl. No. 11/876,719.
USPTO; Office Action dated May 26, 2011 in U.S. Appl. No. 11/876,732.
USPTO; Office Action dated Aug. 8, 2011 in U.S. Appl. No. 11/877,541.
USPTO; Office Action dated Oct. 16, 2009 in U.S. Appl. No. 11/877,582.
USPTO; Advisory Action dated Jul. 11, 2011 in U.S. Appl. No. 11/877,582.
USPTO; Advisory Action dated May 31, 2011 in U.S. Appl. No. 11/877,930.
USPTO; Advisory Action dated May 6, 2011 in U.S. Appl. No. 11/877,966.
USPTO; Office Action dated May 17, 2011 in U.S. Appl. No. 12/940,957, Sep. 24, 2011.
USPTO; Office Action dated Aug. 30, 2011 in U.S. Appl. No. 11/877,550.
CN; Second Office Action dated Jul. 27, 2011 in Application No. 200790048047.3.
USPTO; Advisory Action dated Jul. 19, 2011 in U.S. Appl. No. 11/877,994.
USPTO; Final Office Action dated Aug. 31, 2011 in U.S. Appl. No. 12/951,957.
USPTO; Office Action dated Apr. 14, 2010 in U.S. Appl. No. 11/876,689.
USPTO; Final Office Action dated Dec. 22, 2010 in U.S. Appl. No. 11/876,689.
USPTO; Office Action dated Apr. 1, 2010 in U.S. Appl. No. 11/876,695.
USPTO; Final Office Action dated Dec. 21, 2010 in U.S. Appl. No. 11/876,695.
USPTO; Office Action dated Apr. 28, 2010 in U.S. Appl. No. 11/876,708.
USPTO; Final Office Action dated Dec. 22, 2010 in U.S. Appl. No. 11/876,708.
USPTO; Office Action dated Mar. 29, 2010 in U.S. Appl. No. 11/876,719.
USPTO; Office Action dated Dec. 22, 2010 in U.S. Appl. No. 11/876,719.
USPTO; Office Action dated Sep. 15, 2010 in U.S. Appl. No. 11/876,725.
USPTO; Office Action dated May 26, 2010 in U.S. Appl. No. 11/876,713.
USPTO; Final Office Action dated Dec. 22, 2010 in U.S. Appl. No. 11/876,713.
USPTO; Office Action dated Sep. 3, 2010 in U.S. Appl. No. 11/876,732.
USPTO; Office Action dated Jan. 26, 2011 in U.S. Appl. No. 12/951,957.
USPTO; Office Action dated Jul. 29, 2010 in U.S. Appl. No. 11/877,493.
USPTO; Final Office Action dated Mar. 18, 2011 in U.S. Appl. No. 11/877,493.
USPTO; Office Action dated Jan. 26, 2011 in U.S. Appl. No. 11/877,541.
USPTO; Office Action dated Aug. 31, 2010 in U.S. Appl. No. 11/877,545.
USPTO; Office Action dated Feb. 9, 2011 in U.S. Appl. No. 11/877,550.
USPTO; Office Action dated Jan. 27, 2011 in U.S. Appl. No. 11/877,573.
USPTO; Office Action dated Jul. 1, 2010 in U.S. Appl. No. 11/877,582.
USPTO; Final Office Action dated Mar. 2, 2011 in U.S. Appl. No. 11/877,582.
USPTO; Office Action dated Aug. 9, 2010 in U.S. Appl. No. 11/877,930.
USPTO; Final Office Action dated Mar. 14, 2011 in U.S. Appl. No. 11/877,930.
USPTO; Office Action dated Apr. 13, 2010 in U.S. Appl. No. 11/877,946.
USPTO; Final Office Action dated Dec. 21, 2010 in U.S. Appl. No. 11/877,946.
USPTO; Office Action dated Apr. 15, 2010 in U.S. Appl. No. 11/877,966.
USPTO; Final Office Action dated Dec. 21, 2010 in U.S. Appl. No. 11/877,966.
USPTO; Office Action dated Sep. 1, 2010 in U.S. Appl. No. 11/877,994.
USPTO; Office Action dated Jan. 21, 2011 in U.S. Appl. No. 12/952,009.
EP; Examination Report dated Jan. 18, 2011 in Application No. 7844567.3.
CN; Office Action dated Dec. 2010 in Application No. 200780048044.X.
CN; Office Action dated Mar. 2011 in Application No. 200780048064.7.
CN; Office Action dated Mar. 2011 in Application No. 200780048047.3.
PCT; International Search Report and Written Opinion dated May 14, 2008 in Application No. PCT/US2007/082161.
PCT; International Preliminary Report on Patentability dated Apr. 28, 2009 in Application No. PCT/US2007/082161.
PCT; International Search Report and Written Opinion dated Oct. 10, 2008 in Application No. PCT/US2007/082253.
PCT; International Preliminary Report an Patentability dated Apr. 28, 2009 in Application No. PCT/US2007/082253.
PCT; International Search Report and Written Opinion dated Jan. 15, 2009 in Application No. PCT/US2007/082284.
PCT; International Preliminary Report on Patentability dated Apr. 28, 2009 in Application No. PCT/US2007/082284.
PCT; International Search Report and Written Opinion dated Nov. 6, 2008 in Application No. PCT/US2007/082158.
PCT; International Preliminary Report on Patentability dated Apr. 28, 2009 in Application No. PCT/US2007/082158.

PCT; International Search Report and Written Opinion dated Feb. 18, 2008 in Application No. PCT/US2007/082351.
PCT; International Preliminary Report on Patentability dated Apr. 28, 2009 in Application No. PCT/US2007/082351.
PCT; International Search Report and Written Opinion dated May 27, 2008 in Application No. PCT/US2007/082358.
PCT; International Preliminary Report on Patentability dated Apr. 28, 2009 in Application No. PCT/US2007/082358.
PCT; International Preliminary Report on Patentability dated Apr. 28, 2009 in Application No. PCT/US2007/082288.
How PGP Works, http://www.pgpi.org/doc/pgpintro/.
Princeton University Wordnet; http://wordnetweb.princeton.edu/perl/webwn?s=event; accessed Dec. 19, 2010.
USPTO; Advisory Action dated Apr. 1, 2011 in U.S. Appl. No. 11/876,689.
USPTO; Final Office Action dated May 24, 2011 in U.S. Appl. No. 11/876,725.
USPTO; Final Office Action dated May 11, 2011 in U.S. Appl. No. 11/877,545.
USPTO; Final Office Action dated May 11, 2011 in U.S. Appl. No. 11/877,994.
USPTO; Office Action dated Aug. 30, 2011 in U.S. Appl. No. 11/877,573.
USPTO; Office Action dated Oct. 5, 2011 in U.S. Appl. No. 12/939,070.
USPTO; Office Action dated Sep. 15, 2011 in U.S. Appl. No. 11/877,582.
USPTO; Office Action dated Oct. 17, 2011 in U.S. Appl. No. 12/940,930.

* cited by examiner

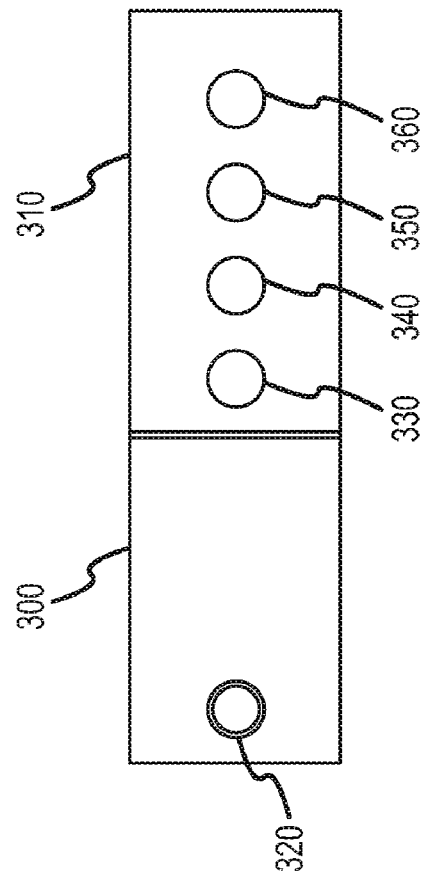
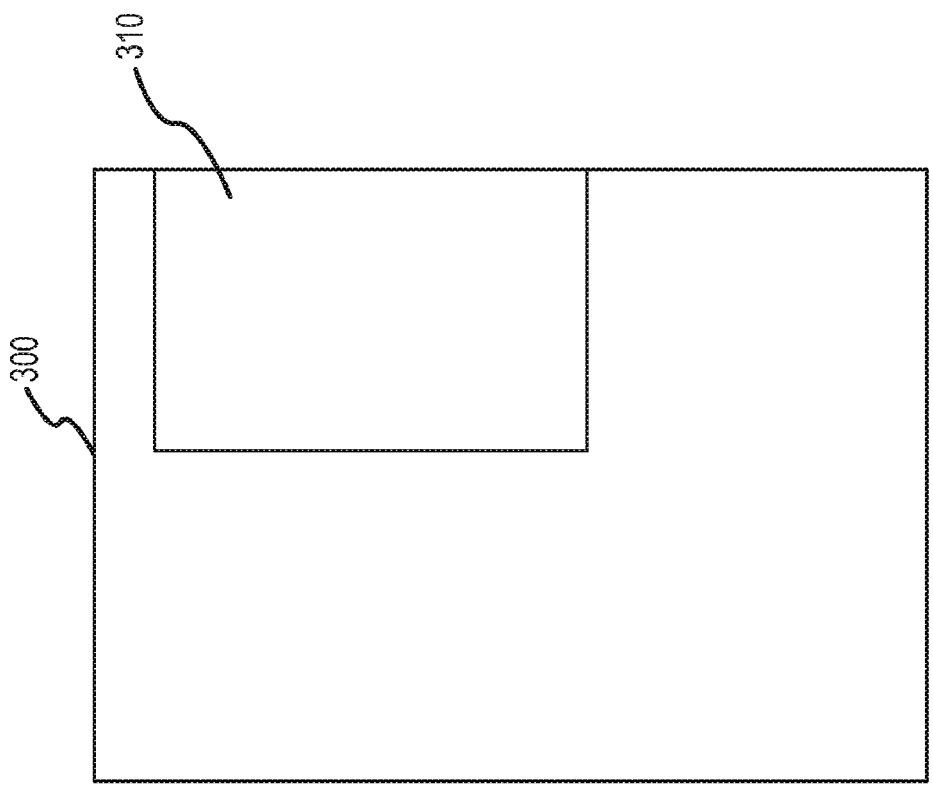
FIGURE 3B
FIGURE 3A

SYSTEMS AND METHODS FOR ADAPTER-BASED COMMUNICATION WITH A MEDICAL DEVICE

CROSS-REFERENCE TO RELATED APPLICATION

This application claims priority to U.S. Provisional Patent Application Ser. No. 60/862,743, filed Oct. 24, 2006, the disclosure of which is incorporated by reference in its entirety.

STATEMENT REGARDING FEDERALLY SPONSORED RESEARCH OR DEVELOPMENT

Not applicable.

NOTICE OF INCLUDED COPYRIGHTED MATERIAL

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. All trademarks and service marks identified herein are owned by the applicant.

DESCRIPTION OF THE INVENTION

1. Field of the Invention

The present invention relates to systems and methods for medical data interchange, and more particularly, to systems and methods for monitoring medical devices through wired connections.

2. Background of the Invention

Historically, patient medical care was often provided for in the patient's home or some other environment apart from a clinical setting. Physicians, midwives, or other healthcare providers would make house calls, observe patient symptoms, formulate diagnoses, and provide treatment. As the state of the art of health care evolved over time, the number of house calls made by healthcare professionals diminished. In large part, health care providers conducted fewer and fewer house calls because it became impractical to bring bulky medical diagnosis and test equipment to the patient. Likewise, it was not cost effective or intellectually feasible for patients to purchase and operate the complicated and expensive medical machines in a home setting. Therefore, the health care model changed dramatically, emphasizing patient visits to health care facilities where an assortment of state-of-the-art test equipment would be available to assist doctors in more accurately assessing and treating patients. This meant that patients were now expected to come to the doctor, rather than the other way around.

Innovations in electronics in the last twenty years have made available a large number of more affordable and patient-operable medical devices that obviated, at least in part, the need for the patient to go to a facility each time a medical test or device checkup was required. Size and expense were not the only factors making this possible; since the new devices provided sophisticated processing in smaller form factors, the technical complexity required to operate the devices were reduced to a level that would not overwhelm a layperson's knowledge. Unfortunately, although portable medical devices such as blood glucose meters now allow patients to perform tests outside the context of medical facilities, patients still need to meet with health care providers to discuss the results obtained.

Some medical devices include ports to allow the communication of data to and from the medical device through a cable or other wired connection. Medical devices that communicate through such wired connections allow healthcare providers to monitor the operation of the medical device, as well as to optionally monitor a patient's biological and biometric information, the patient's behavior, and other information pertinent to the treatment of the patient. However, the manner in which medical devices communicate data varies depending on the type and manufacturer of the device, and therefore, proprietary equipment has been designed to communicate with medical devices only using a specific type of wired connection based on the type of medical device being used.

Medical devices can communicate through a wide range of wired connections. In the context of this application, "wired connection" generally refers to any physical connection that a medical device can communicate through. For example, "wired connections" can also refer to a waveguide, such as an optical fiber. Other wired connections that can be used by various medical devices include various sizes of tip and sleeve (TS), tip, ring, and sleeve (TRS), and tip, ring, ring, and sleeve (TRRS) connections. Such connections are also commonly referred to as "RCA plugs," "phone plugs," and "stereo jacks" and commonly include plug diameters of 2.5 mm and 3.5 mm when used with medical devices. Other wired connections, such as serial peripheral interface bus (SPI) connections, universal serial bus (USB) connections, RS-232 serial connections, Firewire (IEEE 1394) and Ethernet connections may also be used. A wired connection can also include any soldered electrical connection, trace on a circuit board, or other physical connection. Each of these connections vary not only in the physical structure of the connection, but also in the communication protocols used to transfer data. It would thus be desirable to have the capability to communicate with a variety of medical devices regardless of the specific wired connection they use.

To make patient monitoring more convenient, Remote Patient Monitoring (RPM) was developed. Remote Patient Monitoring (RPM) generally refers to monitoring one or more conditions of a patient without requiring the patient to visit a hospital, doctor's office, or other healthcare facility. RPM can increase the efficiency and effectiveness of providing care to patients while reducing costs. RPM can be particularly useful when a patient has a long-term or chronic disease that would otherwise require frequent visits to a healthcare facility and/or where a patient's treatment regimen should be modified based on changed patient conditions that are monitored by one or more medical devices, such as a pacemaker or glucose meter. For example, Type-I Diabetes patients (a lifelong condition) use glucose meters to monitor their blood sugar level to assist in determining when to take insulin—it would be desirable if such information could be quickly, easily, and effectively relayed to a heath care provider for review and analysis.

Conventional RPM generally involves the use of a specific monitoring device installed in a patient's home. The device collects data concerning the patient's condition and relays the data to a healthcare provider. Some conventional systems require a patient to manually enter the data. For example, a diabetes patient using a conventional system for RPM may be required to sample their blood sugar level using a glucose meter, take note of the reading, and then manually enter the level in the conventional system. There are drawbacks with these conventional devices. Because of their complexity and proprietary interfaces, many are very expensive, which reduces the cost-savings benefit of RPM. Additionally, they often require a land-line connection (such as phone or VPN) to transmit data and/or are physically bulky/heavy and therefore difficult to transport. Furthermore, conventional systems are often unable to provide data to healthcare providers quickly where data must be manually entered by a patient, which can reduce the level of benefit the patient receives from RPM. What is needed, then, is a system to allow health care providers to freely access patient-related health data, enabling the provider to conduct a virtual house call. What is also needed is a portable device and system that interoperates with a variety of medical devices utilizing a broad range of wired connections to receive medical data, and provides for management and transport of that data to a healthcare provider.

SUMMARY OF THE INVENTION

Methods and systems according to the present invention may operate in conjunction with any wired connection, including those described above, and may operate in conjunction with multiple wired connections. In exemplary embodiments, methods and systems according to the present invention may be configured to receive medical device data transmitted in any format and from any medical device. A system according to one aspect of the present invention comprises a processor, a device interface, a data relay transceiver, and a memory coupled to the processor and storing instructions. Those of skill in the relevant arts understand that the data relay transceiver referenced herein may comprise a receiver, a transmitter, or both a receiver and transmitter, and may receive and/or transmit electrical signals, radio frequency signals, modulated light signals, sonic signals, or other signals propagated through a suitable medium. The processor executes the instructions in the memory to receive data from a medical device through a wired connection using the device interface (which gathers data concerning the patient's condition), where the data is received through an adapter coupled to the device interface and that communicates with the medical data interchange device using a first communication format and with the medical device using a second communication format. The processor further executes the instructions in the memory to transmit the data to an intermediary device using the data relay transceiver. This system can be implemented in a small, portable unit that is easy for a patient to transport. For example, the unit could be the size of a cell phone or contained within a cell phone, or could be a small accessory device that is connected to the medical device, such as in a container in which the medical device is also situated. As with the method described above, the system can optionally communicate with multiple medical devices, regardless of the type of wired connection or communications protocol utilized by each of the medical devices, and can retransmit (and optionally reformat) data from the medical device(s) to any desired recipient using any suitable frequency(ies) and communication protocol(s). The adapter can be removably coupled to the medical data interchange device to allow different adapters configured to communicate with different medical devices to be used with a single medical data interchange device.

A system according to another aspect of the present invention comprises a processor, a device interface, a data relay transceiver, and a memory coupled to the processor and storing instructions. The processor executes the instructions in the memory to receive data from a medical device through a wired connection using the device interface where the data is received through an adapter coupled to the device interface and that communicates with the medical data interchange device using a first communication format and with the medical device using a second communication format. The processor further executes the instructions in the memory to encrypt the data and to transmit the data to an intermediary device using the data relay transceiver. The encryption can be implemented using combinations of public and private keys, and allows sensitive medical data for a patient to be securely transmitted to the intermediary device and/or medical data server without being viewed by unintended recipients.

Embodiments of the present invention may be used to monitor any appropriate medical device from essentially any location from which a communications signal can be sent and received. This enables patients to enjoy an active lifestyle by not being tied to medical device monitoring equipment that is difficult or impossible to transport or having to routinely visit health care facilities. The present invention can be used to monitor any amount and type of data from any medical device.

The present invention can also be used for a variety of other monitoring purposes. For example, the present invention can be used to monitor a blood alcohol monitor, alcohol breathalyzer, or alcohol ignition interlock device to help insure a driver does not operate a motor vehicle under the influence of alcohol or other substance. The present invention can also be used in conjunction with a Global Positioning System (GPS) or other geolocation device to monitor the position of a patient. The present invention may also be used in a wide variety of military applications, such as remotely monitoring devices tracking the health status of soldiers on a battlefield in real-time in order to quickly dispatch aid to wounded soldiers. The present invention may be used to remotely monitor a chemical, biological agent, or radiation sensor carried by a soldier to detect an attack by unconventional weaponry.

Both the foregoing summary and the following detailed description are exemplary and explanatory only and are not restrictive of the invention.

BRIEF DESCRIPTION OF THE DRAWINGS

A more complete understanding of the present invention may be derived by referring to the detailed description and claims when considered in connection with the following illustrative figures.

FIGS. 3A and 3B depict top and rear views, respectively, of an external casing for a medical data interchange device according to various aspects of the present invention.

DETAILED DESCRIPTION OF EXEMPLARY EMBODIMENTS

Figure 1:
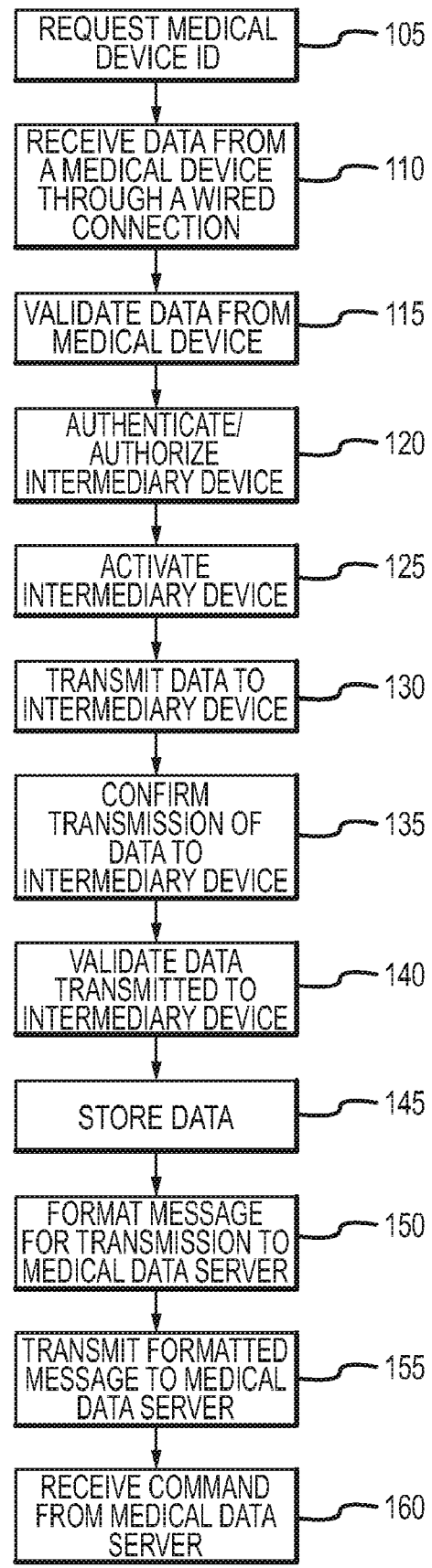
FIG. 1 is a flow diagram depicting an exemplary process for medical data interchange according to various aspects of the present invention.

An exemplary method according to an aspect of the present invention is depicted in FIG. 1. In this method, an identifier is requested from a medical device (105), and data from the medical device is received (110) and validated (115) through a wired connection. An intermediary device such as a mobile phone or personal digital assistant is authenticated (120) and activated (125). The data is transmitted by the medical device to the intermediary device (130) and the transmission to the intermediary device is confirmed (135) and validated (140). The data is stored (145) in the intermediate device. A message is formatted (150) and transmitted to a medical data server (155). Optionally, a command can be received from the medical data server (160) and optionally relayed from the intermediary device. Any combination and/or subset of the elements of the method depicted in FIG. 1 may be practiced in any suitable order and in conjunction with any system, device, and/or process. The method shown in FIG. 1 can be implemented in any suitable manner, such as through software operating on one or more computer systems. Exemplary systems for performing elements of the method shown in FIG. 1 are discussed later in this description.

Request Medical Device Id

In the exemplary process according to aspects of the present invention depicted in FIG. 1, an identifier is requested from a medical device providing the data to be monitored (105). Any suitable identifier may be provided, such as the serial number of the medical device and/or a numeric, alphabetic, alphanumeric, or symbolic identifier. The medical device identifier can be used to determine whether the correct medical device is being monitored. The medical device identifier can also be used to determine the manufacturer, model, type, characteristics, or other information pertinent to the medical device and/or the patient(s) it monitors. The medical device identifier may be received passively, such as from a medical device that automatically includes its identifier as part of its telemetry broadcast. Alternatively, the medical device can be polled to request the medical device identifier. The medical device identifier need not be requested from the medical device each time the medical device is being monitored. For example, the medical device identifier may be stored in a storage medium for future reference.

Receive Data from a Medical Device Through a Wired Connection

In the exemplary method shown in FIG. 1, data is received through a wired connection from the medical device (110). As stated previously, a "wired connection" in the context of this application refers generally to any physical connection that allows communication between two devices. Wired connections thus include, without limitation: tip and sleeve (TS), tip, ring, and sleeve (TRS), and tip, ring, ring, and sleeve (TRRS) connections; serial peripheral interface bus (SPI) connections; universal serial bus (USB) connections; RS-232 serial connections, Ethernet connections, optical fiber connections, and Firewire connections. Data from a medical device may be received using any number and combinations of such connections, as well as any other type of connection. Additionally, medical device may communicate data through a wired connection using any suitable format and communications protocol.

Systems implementing the method depicted in FIG. 1 are preferably small, light, and portable, allowing patients monitored by medical devices to lead active lifestyles without being forced to remain close to a non-portable system receiving the data from the medical device. Data can be received from any medical device, such as a blood glucose meter, a pacemaker, a blood pressure monitor, an insulin pump, a pulse oximeter, a holter monitor, an electrocardiograph, an electroencephalograph, a blood alcohol monitor, an alcohol breathalyzer, an alcohol ignition interlock, a respiration monitor, an accelerometer, a skin galvanometer, a thermometer, a patient geolocation device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) monitor, an international normalized ratio (INR) monitor, a tremor sensor, a defibrillator, or any other medical device.

A medical device that includes a combination of different medical devices (such as those listed previously) may be monitored in accordance with the present invention. The medical device can be partially or completely implanted in a patient, such as in the case of a pacemaker. Data from the medical device can be received through any number of other relay devices, such as routers, hubs, bridges, switches, and modems. Where the medical device is completely implanted in the patient, such relay devices can receive data from the medical device wirelessly and retransmit the data through a wired connection. The medical device may also be located externally to a patient. The medical device may be connected to a patient (for example, through one or more electrodes), or operate independent of any coupling to a patient, such as a scale. The medical device may also operate in conjunction with a temporary interfacing with a patient, such as the case of the cuff of a blood pressure monitor encompassing the arm of a patient to take a reading.

Figure 2A:
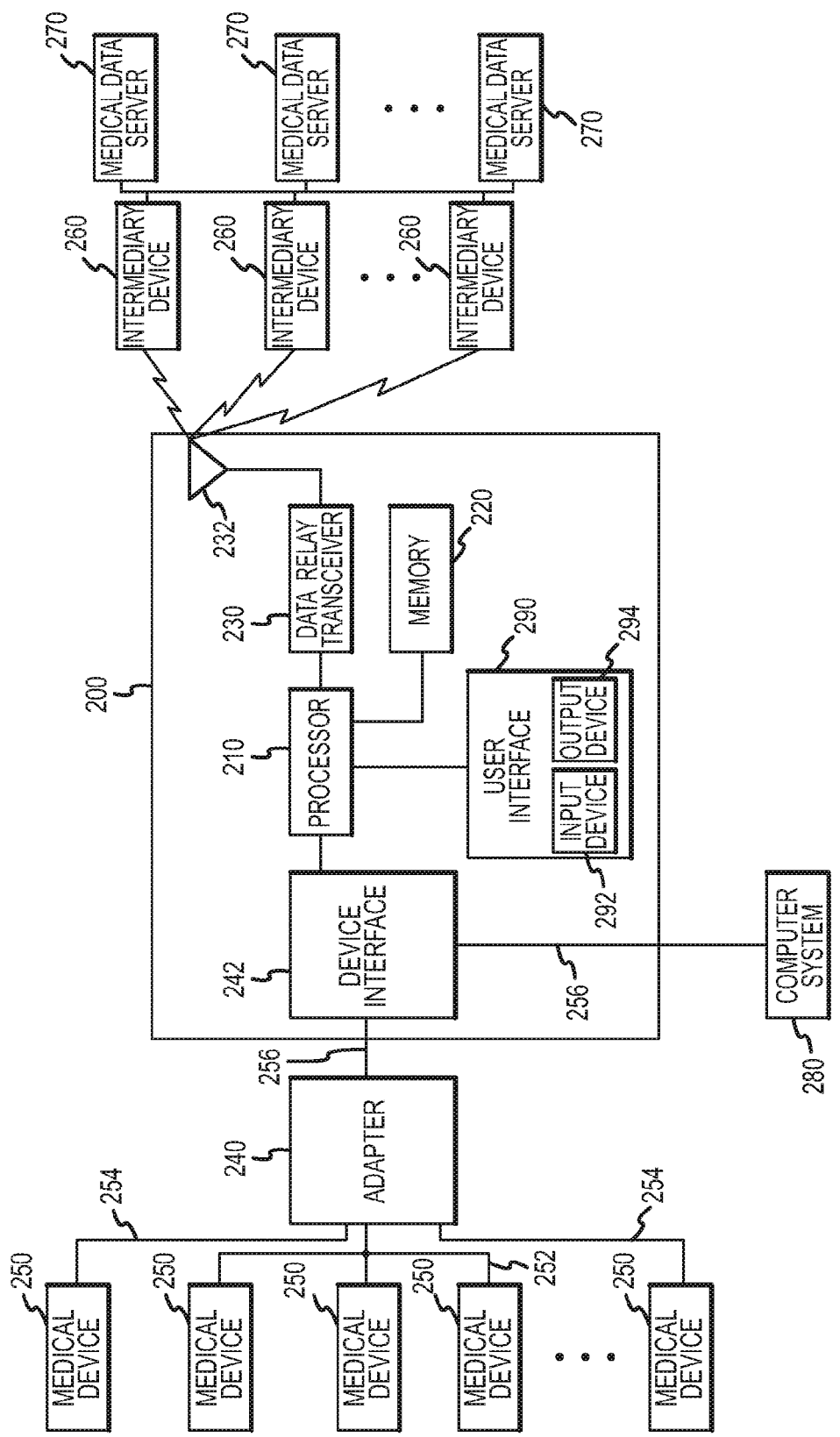
FIG. 2A is a block diagram depicting an exemplary system for medical data interchange according to various aspects of the present invention.
Figure 2B:
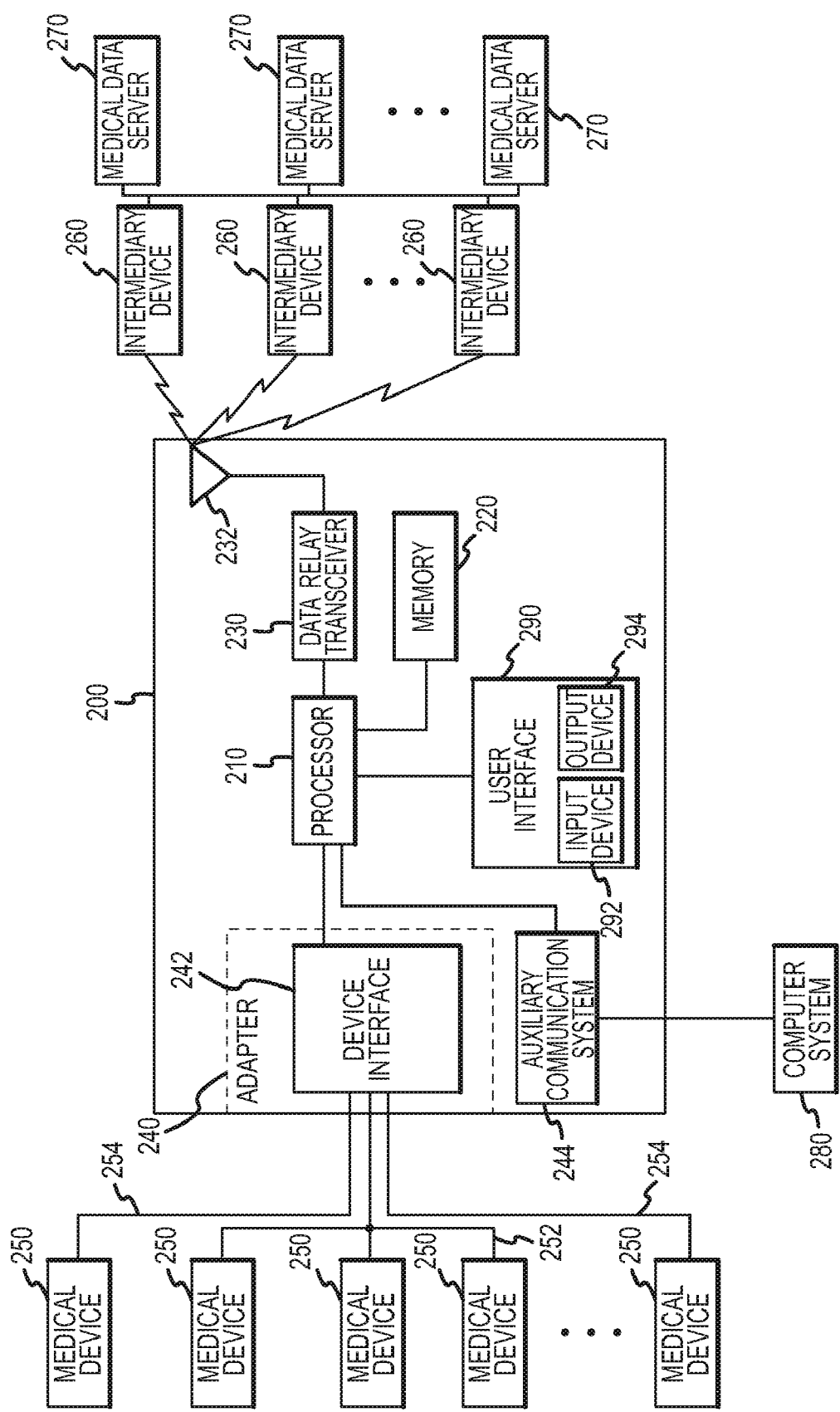
FIG. 2B is a block diagram depicting another exemplary system for medical data interchange according to various aspects of the present invention.
Figure 2C:
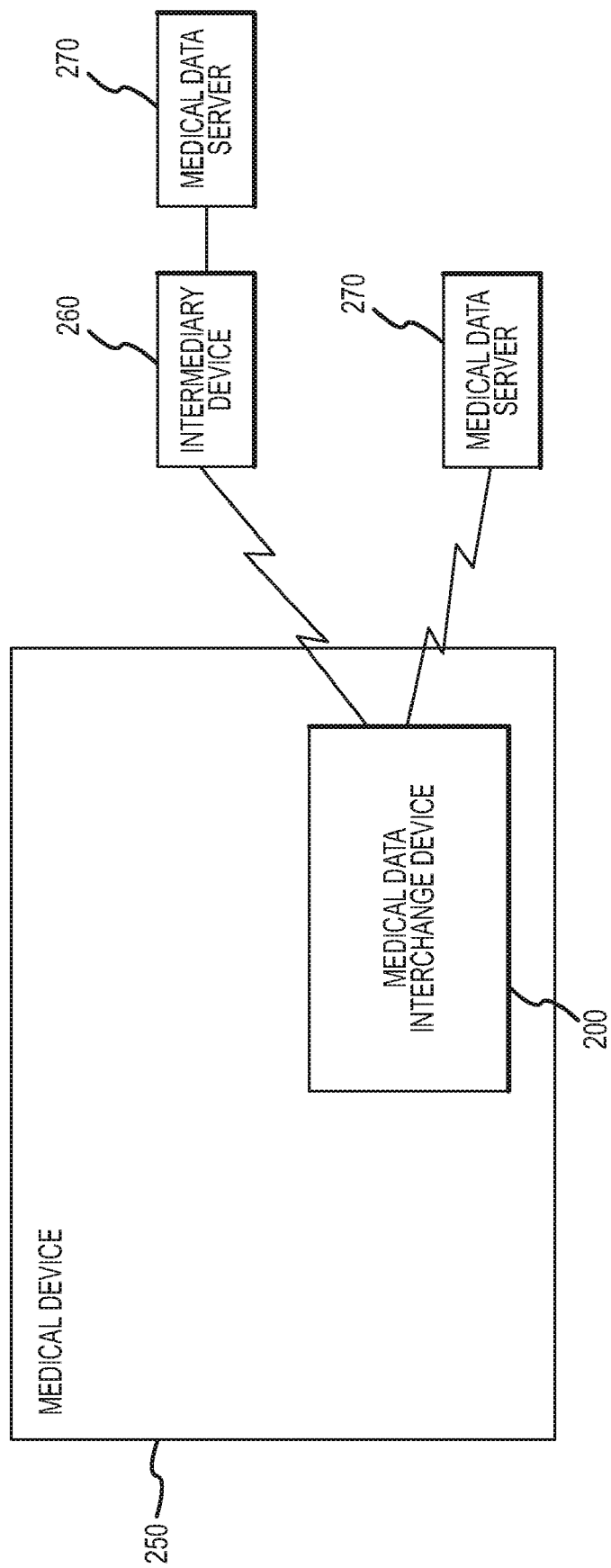
FIG. 2C is a block diagram depicting yet another exemplary system for medical data interchange according to various aspects of the present invention.

The medical device data can be received by any person, system, device, or other suitable recipient. The exemplary method in FIG. 1 may be practiced manually by a human being, automatically by a device, or a combination of the two. Exemplary devices for performing the method illustrated in FIG. 1 are depicted in FIGS. 2A, 2B, and 2C, and are discussed in detail below.

Data can be received directly from a medical device. For example, some medical devices such as glucose meters have ports that allow data to be communicated through a cable. As mentioned previously, a medical device can also provide data using another device, system, or other entity. In one embodiment of the present invention, for example, a medical device provides data through a serial port (a wired connection) to a computing device. The computing device is in turn connected to an Ethernet router or hub. The data can thus be received through an Ethernet connection from the router or hub. In another exemplary embodiment of the present invention, a human patient retrieves data from the medical device and then provides the data through a keypad, microphone, or other suitable input device.

The medical device data can be received from a plurality of different medical devices, where each medical device may perform any combination of functions. For example, data from a glucose meter, blood pressure monitor, and combination scale/height measuring device each transmitting data in different formats and through different wired connections may each be received in accordance with the present invention. In the case where a plurality of medical devices transmits data in response to a request for data, each device in the plurality of devices can be sent such a request separately. Alternatively, a plurality of medical devices automatically transmitting data in the same format, and potentially at the same time (such as in the case of multiple devices of the same type and/or from the same manufacturer) can be received in accordance with the present invention by, for example, using separate wired connections. When data has been received from a plurality of medical devices, in one embodiment, a list of the medical devices may be displayed on a user interface, and optionally, the user may be prompted to select one, all, or none of the plurality medical devices, whose data is desired to be transmitted to the medical data server. The data for the selected set of medical devices is then relayed as described with alternate embodiments as described herein. Any other suitable method for receiving data from a plurality of medical devices may also be used in conjunction with the present invention.

Any type of data may be received from a medical device. For example, the data may include information regarding a patient, such as the patient's biological and biometric information, the patient's behaviors, results of analysis of physical patient parameters, and information regarding the patient's environment. For example, a medical device such as a glucose meter could provide data regarding a patient's current (or last measured) blood glucose level, the date and time the patient last used the glucose meter, and the current temperature or other environmental factors that might affect a glucose test. Other possible environmental parameters that may be included in the data received from a medical device include a battery charge level, a temperature, a barometric pressure, a code relating to an accessory for the medical device, a data validity measurement, an elapsed time since a previous reading by the medical device, a test result parameter, a signal-to-noise parameter, and a quality of service (QoS), and combinations thereof. Data received from a medical device may also include any other suitable information, such as diagnostic information regarding the medical device.

The medical device data may provide data relating to a single patient or multiple patients. In the case where a single medical device provides data regarding multiple patients, the data can be identified with an individual patient either in the data received by medical device (such as by using a patient identifier) or through processing in accordance with the present invention.

The medical device can provide the data in any format. Different medical devices from different manufacturers often use different formats for providing data. For example, data from a glucose meter may be provided in a series of fixed-length data records followed by a terminator indicator (such as a null or other predefined character) and/or a checksum for validating the data. Any type of data may be provided. In the case of a glucose meter, the data may include one or more readings of a patient's blood glucose level and the date and time each reading was taken. The medical device identifier discussed previously may be used to determine a specific data format used by a medical device. Alternatively, a data format may be specified by a user or selected by analyzing the format of the data received and comparing it to a set of known medical device data formats.

Validate Data

In the exemplary process shown in FIG. 1, the data from the medical device is validated (115). The data from the medical device can be validated in any suitable manner to achieve any result. For example, the data from the medical device may be validated to ensure it was transmitted properly and completely. The medical device data may also be validated to ensure it was provided from a specific medical device or particular type of medical device. The data may also be validated to ensure that fields in the data correspond to predetermined values and/or are within certain thresholds or tolerances. Any number, code, value or identifier can be used in conjunction with validating the medical device data. For example, the data can be validated by analyzing a medical device serial number, a medical device identifier, a patient identifier, one or more parity bits, a cyclic redundancy checking code, an error correction code, and/or any other suitable feature.

Authenticate/Authorize Intermediary Device

In the exemplary method depicted in FIG. 1, an intermediary device receiving the data is authenticated (120). In the context of the present invention, the intermediary device includes any type of system or device capable of receiving the medical device data in any manner. Such intermediate devices may include, for example, personal computers, laptops, personal digital assistants, routers, hubs, bridges, switches, modems, and mobile computing devices. The intermediary device may process the data in any manner, and can transmit some or all of the data to another recipient, such as a medical data server. For example, but not by way of limitation, the intermediary device may include a personal computer or a mobile computing device, such as a laptop computer, a mobile wireless telephone, or a personal digital assistant (PDA). In an exemplary embodiment of the present invention, the intermediate device further includes software for receiving the medical device data, formatting a message based on the data, and transmitting the formatted message to a medical data server. Such software can operate on any suitable mobile computing device and with any computer operating system. The intermediary device may also include any number of other systems and devices suitable for receiving data from the medical device, processing the data, and/or transmitting the data to a medical data server. Further discussion regarding exemplary embodiments of intermediary devices is presented later in this description.

The intermediary device can receive the data directly from the medical device, or from one or more other devices. In one exemplary embodiment of the present invention, the intermediary device comprises a mobile computing device and is configured to receive data from one or more medical devices directly through one or more wired connections. In another exemplary embodiment of the present invention, the medical device transmits the data to a first device through a wired connection, which in turn transmits the medical device data to the intermediary device (wirelessly or through a wired connection).

The intermediary device may be authenticated to achieve any result. For example, transmission may be restricted only to authenticated devices operating as part of the present invention. Authentication can also prevent sensitive medical data from being viewed by unintended recipients. The intermediary device may also be authenticated to verify the intermediary device is able to receive, process, and/or transmit the medical device data to a medical data server. During authentication, the authenticated device or devices may also be remotely commanded, and such commands may include steps that configure devices to interoperate with components of the present invention. For example, but not by way of limitation, such steps may include the downloading of software applications, applets, embedded operating code, and/or data.

The intermediary device can be authenticated in any manner. For example, an intermediary device can be authorized to receive data from one or more medical devices using an authorization code. The authorization code can be any number, code, value or identifier to allow the intermediary device to be identified as a valid recipient of the data from the medical device. In one exemplary embodiment of the present invention, an intermediary device stores an authorization code and broadcasts the authorization code in response to a request for authorization. Unless the authorization code matches a code stored by the transmitter of the medical device data (such as the medical device itself or another transmission device), the medical device data is not transmitted to the intermediary device. Transmission of the medical device data to the intermediary device need not necessarily be predicated upon successful authentication of the intermediary device, however. For example, where the medical data is related to a medical emergency, the medical data could be transmitted to any suitable intermediary device within range, whether or not any intermediary device is actually able to be authenticated or authorized to receive the data.

In another exemplary embodiment of the present invention, an intermediary device receiving the medical device data using a wireless network protocol (such as Bluetooth) is authenticated based on whether the intermediary device advertises one or more services. In this context, advertised services reflect functions, utilities, and processes the intermediary device is capable of performing. The intermediary device broadcasts indicators of this functionality, thus "advertising" them to other systems and devices. In the present exemplary embodiment of the invention, unless the intermediary device advertises a service that is identifiable with the operation of the present invention (i.e. a process capable of broadcasting the medical device data to a medical data server, for example), the intermediary device is not authenticated and thus the medical device data is not transmitted to the intermediary device.

Activate Intermediary Device

In the exemplary process depicted in FIG. 1, the intermediary device can be activated (125) prior to transmitting the medical device data to the intermediary device. Many devices, particularly mobile computing devices running on batteries, employ power-saving features to conserve battery life when not in use. In the case where an intermediary device is in a power-saving or standby mode, it may be necessary to activate the intermediary device before it can receive the medical device data. The intermediary device can be activated in any suitable manner. For example, a signal configured to activate the device may be transmitted to prepare the intermediary device to receive the medical device data.

Transmit Data to Intermediary Device

The medical device data is transmitted to the intermediary device (130) in the exemplary process depicted in FIG. 1. The data can be transmitted in any suitable manner. In one exemplary embodiment of the present invention, the medical device data is transmitted to the intermediary device using a wired connection, such as an RS-232 serial cable, USB connector, Firewire connector, or other suitable wired connection. The medical device data can also be transmitted to the intermediary device wirelessly using a wireless transmitter. Any suitable method of wireless communication can be used to transmit the medical device data, such as a Bluetooth connection, infrared radiation, Zigbee protocol, Wibree protocol, IEEE 802.15 protocol, IEEE 802.11 protocol, IEEE 802.16 protocol, and/or ultra-wideband (UWB) protocol. If desired, the medical device data could be transmitted to the intermediary device using both a wired and wireless connection, such as to provide a redundant means of communication, for example.

Any amount of medical device data can be transmitted to the intermediary device in any manner. For example, data from the medical device can be transmitted to the intermediary device in real-time as it is measured, or medical device data can be stored (such as in a memory storage device) for a period of time before being transmitted to the intermediary device. In some cases, for example, it may be more efficient to transmit blocks of medical device data at once rather than initiating communication with an intermediary device each time data is available from the medical device. In other cases, the intermediary device may be out of range or otherwise unavailable to receive the medical device data. The medical device data can also be stored for any desired length of time, and/or until a particular event occurs. For example, the medical device data could be stored until it is verified that the intermediary device and/or the medical data server have received the data, allowing the data to be retransmitted if necessary. Data can also be deleted when a data record exceeds a predetermined storage time, and/or the oldest data record is deleted first after a predetermined storage size limit has been reached.

The medical device data can be transmitted to the intermediary device in any format. For example, the data from the medical device can be transmitted to the intermediary device exactly as it is transmitted from the medical device. This would be the case in embodiments of the present invention where the medical device itself is transmitting the data directly to the intermediary device. Alternatively, in embodiments of the present invention where the data is being received from the medical device and then retransmitted to the intermediary device, the medical device data can be reformatted, modified, combined with other data, or processed in any other suitable manner before being transmitted to the intermediary device. For example, the medical device data can be encrypted prior to transmission to the intermediary device, and this encryption may occur at any stage, for instance in the medical device itself or at a stage after being transmitted by the medical device. In cases where the medical device data is being combined with other data and transmitted to the intermediary device, all of the data may be encrypted or simply the medical device data itself. In an alternate embodiment, a digest of the medical data may be encrypted, to digitally "sign" the data contents to verify its authenticity. For example, but not by way of limitation, this digest may be produced by providing the received medical data to a hashing algorithm such as the MD5 or SHA-1 Secure Hashing Algorithm as specified in National Institute of Standards and Technology Federal Information Processing Standard Publication Number 180-1.

Asymmetric encryption algorithms and techniques are well known in the art. See, for example, RSA & Public Key Cryptography, by Richard A. Mollin, CRC Press, 2002, and U.S. Pat. No. 4,405,829, issued Sep. 20, 1983, the disclosures of which are fully incorporated by reference herein for all purposes. In an illustrative example, if two parties (for example, "Alice" and "Bob") wish to communicate securely using public key cryptography, each party begins by generating a unique key pair, where one of the keys is a private key that is kept in confidence by that party, and the other key is a public key that may be publicly distributed, published only to a message recipient, or made available through a public key infrastructure. The key generation step need be done by a party only once, provided that the party's private key does not become compromised or known by another party. If Alice wants to send a message confidentially to Bob, she may use Bob's public key to encrypt the message, and once sent, only Bob can decrypt and view the message using Bob's private key. But if Alice also wanted Bob to have assurance that the message was in fact coming from her, she could further encrypt the message with her private key before sending, then when Bob's private key and Alice's public key are used to decrypt the message, Bob knows for certain that he was the intended recipient and that Alice was the one who originated the message, and Alice knows that only Bob will be able to decrypt and read her message.

Asymmetric cryptography may be utilized to enhance security of certain implementations of the present invention. In an alternate embodiment, data transmitted by a medical device 250 is encrypted with a private key of the medical device user (or optionally with the private key of a health care provider that is operating the medical device), or with a public key of the intended recipient system such as the medical data server 270, or with both keys. The private and/or public keys may be delivered to the medical data interchange device 200 through a wired or wireless connection, allowing the medical data interchange device 200 to be configured for secure operation. In one embodiment, the system or medical data server 270 may request that the public key of the medical device be forwarded to enable decryption of any medical information encoded with the user's private key. In this manner, the data may be authenticated as coming from the actual patient that is desired to be monitored, and optionally, the patient may also be assured that only the intended recipient system or medical device server 270 is capable of decrypting and gaining access to the patient's medical device data.

In an alternate embodiment, encrypted or unencrypted data can be transmitted through an encrypted transmission protocol, such as the wireless encryption protocols (WEP, WPA and WPA2) associated with the IEEE 802.11 wireless protocols or a Bluetooth encryption protocol associated with IEEE 802.15. Any number of other encryption methods can be used to encrypt the medical device data in conjunction with the present invention. The intermediary device may decrypt the medical device data, to allow processing of the data for example. Alternatively, to protect the data from unauthorized viewing, an intermediary device could simply retransmit the encrypted data to the medical data server.

Confirm Transmission of Data to Intermediary Device

The transmission of the medical device data can be confirmed (135) to verify the transmission was successful. The transmission can be confirmed in any suitable manner. For example, the intermediary device can transmit an acknowledgement once the transmission is received, otherwise the transmission can be rebroadcast.

Validate Data Transmitted to Intermediary Device

In the exemplary process shown in FIG. 1, the data transmitted to the intermediary device is validated (115). The data from the medical device can be validated in any suitable manner to achieve any result. For example, the data from the medical device may be validated to ensure it was transmitted properly and completely. The medical device data may also be validated to ensure it was provided from a specific medical device or particular type of medical device. The data may also be validated to ensure that fields in the data correspond to predetermined values and/or are within certain thresholds or tolerances. Any number, code, value or identifier can be used in conjunction with validating the medical device data. For example, the data can be validated by analyzing a medical device serial number, a medical device identifier, a patient identifier, one or more parity bits, a cyclic redundancy checking code, an error correction code, and/or any other suitable feature.

Store Data

The intermediary device may store the medical device data (145). The intermediary device may store the data in any suitable manner, such as by using a memory storage device. Any portion or amount of medical device data (or other forms of information) received or generated by the intermediary device may be stored for any length of time. The data may be stored for a predefined period of time and/or until an event occurs. For example, in one embodiment of the present invention the data is stored by the intermediary device until the data has been transmitted to the medical data server. In another embodiment, data is stored by the intermediary device until a predetermined data transmission record size has been reached, so as to reduce communication charges that may accrue during transmission. In yet another embodiment, the intermediary device stores the data until an acknowledgment from the medical data server is received, where the acknowledgment indicates that the stored data has been received by the medical data server. The medical data may be stored in any desired file format, as well as in an encrypted or decrypted state.

Format Message for Transmission to Medical Data Server

In the exemplary method according to an aspect of the present invention depicted in FIG. 1, a message is formatted for transmission to the medical data server. The message can originate from any entity operating in conjunction with the present invention. For example, the message may be created by the intermediary device, a device transmitting the medical device data to the intermediary device, or the medical device itself. The message can include some or all of the medical device data, as well as any other information useful to the medical data server. Multiple messages can be formatted to include any desired amount of medical device data. For example, in the case of data from a glucose meter, multiple messages may be formatted to each include a single glucose reading, or a single message could be formatted to include the last ten glucose readings taken by the meter. The message can include any other desired data from any suitable source. For example, real-time data from a medical device may be included in a message along with previously-transmitted data from the stored by the intermediary device creating the message. The message (in whole or in part) may be encrypted to protect the contents of the message from unintended viewers and/or the privacy of the patient being monitored.

The message provides the medical device information to the medical data server in a format the medical data server can recognize and utilize. The message can thus be formatted to only include portions of the medical device data needed by the server and/or additional information about a patient, the medical device, and/or the treatment regimen. The message can be of any desired format. For example, the message can be included in a file having a tokenized format such as standard ASCII text format, or any other suitable standardized file format, such as an MS Word document, MS Excel file, Adobe PDF file, or binary picture file (JPEG, bitmap, etc.). The data within such a file can be ordered in any manner and have any suitable delimiters, notations, or other features. For example, a list of multiple glucose level readings in a text file message could be provided chronologically by when the readings were taken, with comma or tab delimiters to denote the start and end of each reading. The message may also have a unique and/or propriety format.

The format of the message can also be based on the method by which the message is transmitted to the medical data server. For example, where the message is transmitted to the medical data server using a wireless mobile telephone such as a cellular phone, the message can be formatted as an SMS text message. Similarly, the message may be formatted as an XML record, email, and/or facsimile. The message can include multiple formats and/or multiple messages may be formatted having different formats for transmission in a variety of methods or to a variety of recipient medical data servers.

Transmit Formatted Message to Medical Data Server

The message is transmitted to a medical data server (160) to allow the medical device data to be analyzed and processed. The message can be transmitted to a single medical data server, or to a plurality of medical data servers. The medical data server can be any suitable recipient of the medical device data. For example, the medical data server can be a computer system or other device as well as a human recipient (such as a doctor, nurse, or other healthcare provider). The message may be transmitted to the medical data server by any entity operating in conjunction with the present invention, and need not be the same entity that received the medical data or formatted the message. For example, the message may be transmitted to the medical data server by the intermediary device, any device transmitting or receiving the medical device data, or the medical device itself.

The message can be transmitted to the medical data server in any suitable manner. For example, the message can be transmitted to the medical data server through a wired connection, such as a telephone line, fiber optic cable, and/or coaxial cable. The message may also be transmitted wirelessly using any suitable wireless system, such as a wireless mobile telephony network, General Packet Radio Service (GPRS) network, wireless Local Area Network (WLAN), Global System for Mobile Communications (GSM) network, Enhanced Data rates for GSM Evolution (EDGE) network, Personal Communication Service (PCS) network, Advanced Mobile Phone System (AMPS) network, Code Division Multiple Access (CDMA) network, Wideband CDMA (W-CDMA) network, Time Division-Synchronous CDMA (TD-SCDMA) network, Universal Mobile Telecommunications System (UMTS) network, Time Division Multiple Access (TDMA) network, and/or a satellite communication network. The message may be transmitted using any suitable combination of multiple wired and wireless communication methods. The transmission method selected to transmit the message to the medical data server can be chosen according to any desired criteria. For example, one or more transmission methods can be selected from a plurality of possible transmission methods to send the message based on each method's cost, time required to transmit, reliability, security, or any other suitable factor. Based on such criteria, the message may be stored until there is a suitable opportunity to transmit the message. For example, the message may be stored until an evening or weekend rate is available on a communications network.

Receive a Command from Medical Data Server

In addition to receiving the medical device data, the medical data server can transmit a command (160). The command can be received by the intermediary device, the medical device, and/or or any other suitable recipient. Any number of commands of any type may be transmitted by the medical data server. The command can be transmitted using the same variety of wired and wireless methods discussed previously for the transmittal of the formatted message. The command need not be transmitted using the same communication method with which the formatted messages are transmitted to the medical data server.

In one embodiment of the present invention, for example, the medical data server issues a command to reconfigure a software application operating on the intermediary device. In another embodiment, the medical data server issues one or more commands to control the functionality of the medical device. In yet another embodiment, the medical data server issues one or more commands to request that a public encryption key corresponding to the patient using a medical device be forwarded to the medical data server, or that a device associated with the present invention receive a public encryption key corresponding to an intended recipient such as a particular health care service provider or other known destination such as the medical data server. In another embodiment, the medical data server issues one or more commands to cause the medical device to perform a warm reset, a cold restart, or to reset a password.

The commands need not be sent directly to a device they are intended to control. For example, a command could be transmitted to an intermediary device, which in turn retransmits it (unmodified) to the medical device to be controlled. Alternatively, the intermediary device could receive a command from the medical server, analyze the command, and then transmit an appropriately formatted command tailored to the specific medical device to be controlled. In this manner, the medical data server need not be able to generate a command for each and every specific device it wishes to control, rather, it can send a command appropriate to a class of devices (i.e. glucose meters) and the intermediary device will appropriately translate the command to control the medical device. The commands from the medical data server can initiate/run diagnostic programs, download data, request the patient's public encryption key, download the intended recipient's public encryption key, and perform any other suitable function on the intermediary device, medical device, or other devices operating in conjunction with systems and methods of the present invention.

In one embodiment, a user of a medical device may interact with the medical data server, and as a result of such interaction, cause a command to be created by the medical data server and transmitted to the medical device. Such a user may comprise, for example, the patient associated with the medical device or a health care provider that is caring for the patient. In various embodiments, the user may interact with a system that includes the medical data server through a computer interface (e.g. a web browser), a portable digital assistant (PDA), a mobile communication device (such as a cell phone), an emergency medical beacon, a medical data interchange device, an interactive voice response (IVR) function associated with the system, or other suitable interface. In one scenario, for example, the user calls the IVR function through a cellular network or PSTN connection, and in response to guided voice prompts, the user either gives vocal input, button-press inputs such as by DTMF tones, or a combination of methods. Based on the user's inputs to the system, whether by IVR or other means, the medical data server may respond by generating a command that is ultimately transmitted to the medical device or an intermediary device. In one implementation, the medical data server could generate and transmit a command that instructs the medical device to transmit data to the medical data server either directly or through an intermediate device. Such data may represent, for example, medical or historical information regarding a patient or the user of the medical device; medical device diagnostic information; or environmental parameters such as a battery charge level, a temperature, a barometric pressure, a code relating to an accessory for the medical device, a data validity measurement, an elapsed time since a previous reading by the medical device, a test result parameter, a signal-to-noise parameter, or a quality of service (QoS) parameter. In one implementation, in response to user input or input associated with analysis of data uploaded to the medical data server, the medical data server causes a command to be transmitted to the medical device that instructs the device to take action that results in the administration of a prescribed dose of medication to the patient, or a prescribed shock to the patient's heart.

A command from a medical data server can be in any appropriate format and may include any suitable information. For example, a command may include data received from one medical device 250 to be delivered to another medical device 250 through the medical data interchange device 200. In this manner, a variety of medical devices can share data whether or not they are in communication with the medical data interchange device 200.

A command can also originate from an intermediary device 260. For example, a command to program or reconfigure one or more software programs on the medical data interchange device 200 depicted in FIGS. 2A, 2B, and 2C can be provided by an intermediary device 260 to the medical data interchange device 200 through the data relay transceiver 230. A command, as discussed above, may include multiple instructions, applets, or data elements to be processed, such as sections of executable code or interpretable scripts. Additionally, a user can program or configure a software program on any device operating in conjunction with the present invention through a suitable user interface, such as the user interface 290 of medical data interchange device 200.

In any system where commands can be sent remotely, security is always a concern, especially when a wireless implementation may provide an entry vector for an interloper to gain access to components, observe confidential patient data, and control health-sensitive components such as pacemakers and insulin pumps. In any digital data network, it is also possible that commands intended for one recipient may be misrouted to a patient or health care provider that was not the intended recipient of the command. Embodiments of the present invention provide for enhanced security in a remote command system while still allowing flexibility and minimal obtrusiveness.

In one embodiment, a command received by any of the components in FIG. 2A, 2B, or 2C may be authenticated before the command is either acted upon by the destination component, or forwarded to another component in the system. Authentication may be directed to determining (1) whether the command came from a trusted or authorized source and (2) that the recipient is actually the intended recipient of the command. In one implementation, source command authentication is achieved by determining whether the origin of the command is a trusted component or server, and one way to accomplish this determination is analyzing whether a command is properly digitally signed by the originator or some other authentication information is provided that assures the recipient component that the message or command is authentic and the recipient component is actually the intended recipient. In an alternate implementation, destination command authentication is accommodated by examining the contents of the message or an authorization code to determine the intended recipient, or alternatively decrypting the command or a portion of the command to verify the intended recipient.

In one embodiment, when commands are created by a command originator, the originator provides for a means to verify the authenticity and/or validity of the command by at least one of the following methods: (1) encrypting the command with a private key of the command originator; (2) generating a digest of the command (through a method such as a hashing algorithm discussed above) and optionally encrypting the hashed digest with the command originator's private key, or (3) utilizing a symmetric encryption scheme providing an authentication code (such as a cryptographically hashed password) that is compared to previously stored values. Then, when a system component receives the command along with any encrypted or cleartext certification data, the component may determine the command is valid by (1) attempting to decrypt an encrypted command message with the alleged originator's public key, (2) attempting to decrypt an encrypted digest with the alleged originator's public key, and comparing the result to a hashed value of the command, or (3) comparing a cryptographically hashed password for the alleged originator to known pre-stored values, and if a match is found, authorization is granted. As an additional step, if the command were optionally encrypted using the intended patient/provider's public key, then only the recipient is capable of decrypting the command, ensuring that only the truly intended patient's health-care devices were being issued commands, and not an unintended third party. For example, in one embodiment, authenticating the command comprises decrypting at least part of the command using at least one of: a public key associated with the medical data server; a private key associated with a user of the medical device; and a private key associated with the medical device.

Authenticate User Access to Medical Data Server

Figure 9:
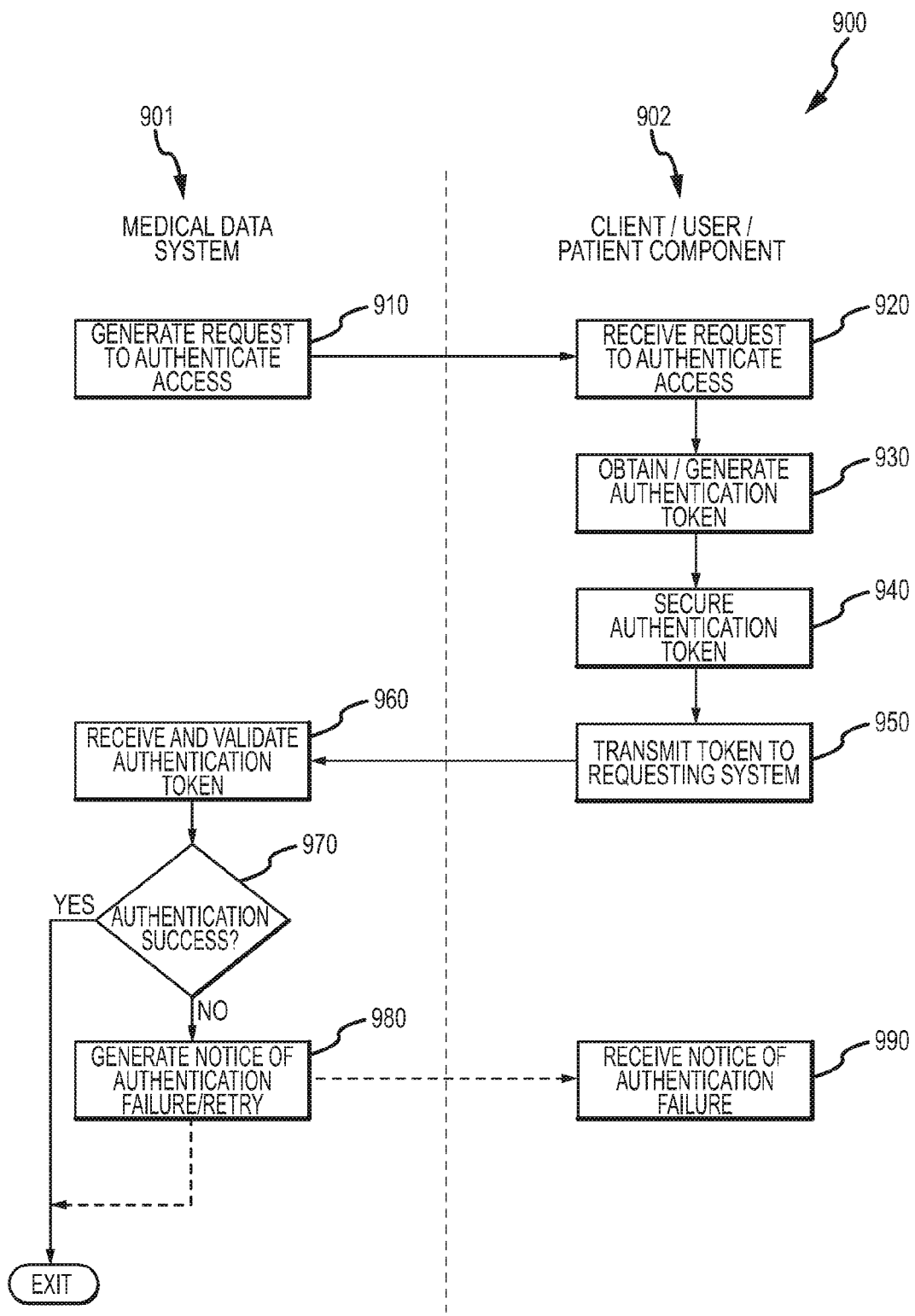
FIG. 9 is a flow diagram showing an exemplary process for authenticating access to a system component of the present invention.

In another embodiment, in regards to the methods described in regards to FIG. 1, it is desirable to ensure that a party attempting to interface with a system such as a medical data server is actually the party believed to be authorized to do so. Turning to FIG. 9, an embodiment is provided that illustrates a method to authenticate user access to the medical data server. A medical data system component 901 such as a medical data server (FIG. 2, 270) generates 910 a request to authenticate access, either on its own accord or as a result of a message received by an alleged patient who is enrolled in the medical service provided by the medical data server. The medical data system 901 then sends a request to authenticate access to a user component 902 of the present invention associated with the client, user, or health care provider, and in one implementation, such component may include the medical data interchange device 200. The user component 902 then receives 920 the request to authenticate access, and generates 930 an authentication token.

In various embodiments, authentication tokens may comprise either simple or complex text strings or data values indicating an account number or other patient identifier that can be matched against an internal patient database by the medical data server. Alternatively, authentication tokens may comprise encoded passwords or other indicia that assert that the entity for whom authentication is requested is genuine. Generation of an authentication token may be accomplished using alternative methods such as entry of a patient identifier, PIN, or password by a patient or healthcare provider after being prompted to do so. Alternatively, a biometric measurement of the patient or healthcare provider could be obtained and the measurement rendered into a digital representation. Once generated, for security purposes the authorization token may be secured 940 by encrypting the token, digesting and encrypting the digest of the token, or cryptographically hashing the token before transmission to the requesting entity such as the medical data system 901 or server. As discussed above in regards to the abovementioned command authentication, in one embodiment, when authentication tokens are created, the originating component of the token may create a certification of validity through at least one of the following methods: (1) encrypting the token with a private key associated with the token originator; (2) encrypting the token with a public key associated with the token requester or destination; (3) generating a digest of the token (through a method such as a hashing algorithm discussed above) and optionally encrypting the hashed digest with the token originator's private key, or (4) providing an authentication code as at least part of the token (such as a cryptographically hashed password) that may be is compared to previously stored values. Then, when a medical data system component 901 receives the token along with any encrypted or cleartext certification data, the component may determine the access is valid by (1) attempting to decrypt an encrypted token with the alleged originator's public key; (2) attempting to decrypt an encrypted token with the alleged originator's public key; (3) attempting to decrypt an encrypted digest with the alleged originator's public key, and comparing the result to a hashed value of the token, pin, code, or password, or (4) comparing a cryptographically hashed password for the alleged originator to known pre-stored values, and if a match is found, authorization is granted.

The medical data system component 901 then receives 960 and analyzes 970 the validity of the authentication token as described above. If examination of the authentication token provides that the token is authentic, such as by comparing the analyzed token data to known, pre-stored values such as the patient or the patient's health care provider's pre-stored hashed password or other identity datum, then access is successful and the process terminates. After analyzing the authentication token or a message containing or associated with the token, the medical data system may determine that access is either permitted or denied, and may communicate 980 this status to the originator of the authentication token 902 who then receives notice of the failure 990. At that point, the system may repeat the process 900, allowing the token originator to attempt access again.

Exemplary Systems

Exemplary systems for use in conjunction with the present invention are depicted in FIGS. 2A, 2B, and 2C. These systems may be used in conjunction with the method described in FIG. 1, as well as with any subset or combination of the elements thereof. The systems shown in FIGS. 2A, 2B, and 2C may also be used in conjunction with any other suitable embodiments of systems and methods for medical device monitoring according to an aspect of the present invention.

The exemplary system depicted in FIG. 2A is a medical data interchange device 200 that includes a processor 210 coupled to a memory 220. A data relay transceiver 230 wirelessly communicates with one or more intermediary devices 260 via antenna 232, which in turn communicates with one or more medical device servers 270 through either a wired or wireless protocol. An external adapter module 240 communicates with one or more medical devices 250. The adapter module 240 also communicates with a device interface 242, as can any number of external devices, such as a computer system 280. The device interface 242 may include any number of wired or wireless connections such as a universal serial bus (USB) connection, serial connection, parallel connection, Firewire connection (such as IEEE 1394), Ethernet connection, or any other suitable connection. Those of skill in the relevant arts also recognize that computer system 280 may also comprise external storage media such as a FLASH drive or a portable hard drive. The exemplary system shown in FIG. 2B includes a modular adapter 240 removably attached to the medical data interchange device 200. In one implementation of this embodiment, the device interface 242 is integrated with the adapter module 240.

The medical data interchange device 200 may include any suitable power connection for powering the interchange device and/or for recharging an energy storage device such as a battery (not shown). The components of the medical data interchange device 200 may receive electrical power from any other type of power supply.

The device interface 242 may establish unidirectional or bidirectional communications with one or more of the medical devices 250 through the adapter 240. The adapter 240 may be located internally or externally to the device interface 242 and/or medical data interchange device 200. In FIG. 2A, for example, the device interface 242 connects to an adapter 240 that is external to the medical interchange device 200, while FIG. 2B depicts the device interface 242 being integrated with the adapter 240.

FIG. 2C depicts an exemplary embodiment of the present invention wherein the medical data interchange device 200 is integrated with a medical device 250. The medical data interchange device 200 can be integrated with the medical device 250 using any number of suitable wired connections (i.e. —soldered connections and/or traces on a printed circuit board) to allow the medical data interchange device 200 to communicate with components in the medical device 250. As with the medical data interchange devices 200 depicted in FIGS. 2A and 2B, the medical data interchange device 200 depicted in FIG. 2C can communicate with any number of intermediary devices 260 and/or medical data servers 270.

The functionality of the medical data interchange device 200 can be implemented in any suitable manner, such as through the processor 210 executing software instructions stored in the memory 220. Functionality may also be implemented through various hardware components storing machine-readable instructions, such as application-specific integrated circuits (ASICs), field-programmable gate arrays (FPGAs) and/or complex programmable logic devices (CPLDs). Systems for medical data interchange according to an aspect of the present invention may operate in conjunction with any desired combination of software and/or hardware components.

Medical Data Interchange Device 200

Referring to FIGS. 3A and 3B, the medical data interchange device 200 depicted in FIGS. 2A and 2B is shown enclosed within a within a case 300. A case holding a system for medical data interchange according to aspects of the present invention may be of any size, shape and configuration. The system (and case enclosing it) is preferably small enough to be easily portable by a patient or person being monitored. For example, the exemplary case 300 depicted in FIGS. 3A and 3B is 3 inches long, 1 inch wide, and 0.5 inches deep. The top and bottom of the case 300 are 0.05 inches thick, while the sides of the case 300 are 0.075 inches thick. The case may be manufactured from any number of materials, such as plastic, metal, wood, composites, and/or any other suitable material. The case 300 shown in FIGS. 3A and 3B, for example, is manufactured from hard plastic.

The case 300 includes a power connection 320 for powering the interchange device 200 and/or for recharging an energy storage device such as a battery. The case 300 also includes an interface module 310 with four separate ports to accommodate different wired connections to the adapter 240, including a serial port interface (SPI) port 330, an infrared input 340, a mini-jack port 350 (i.e. —a 3.5 mm TRS connector), and a super mini-jack port 360 (i.e. —a 2.5 mm TRS connector). The interface module 310 may include any number and type of wired connection ports.

The interface module 310 may include any suitable portion of the medical data interchange device 200. In one embodiment, referring to FIG. 2B, the interface module 310 is an adapter module 240 that includes the device interface 242. The plurality of wired connection ports (330, 340, 350, and 360) are coupled to the adapter 240, which in turn communicates data to the rest of the medical data interchange device 200 through the device interface 242. In this embodiment, the interface module 310 is removably attached to the case 300 to allow different modules 310 to be interchangeably connected to the case 300 to communicate with different medical devices 250.

In another exemplary embodiment, referring again to FIG. 2A, the interface module 310 contains the device interface 242 that couples to an external adapter 240. In this embodiment, the adapter 240 includes one or more connections to one or more medical devices 250. The connections to the medical devices 250 can be through a common wired connection 252, such as a PCI bus, ISA bus, PCI-E bus, SPI, USB, or other common connection. The connections to the medical devices 250 may also be made through individual wired connections to each medical device 254. The adapter 240 can communicate with any number of medical devices 250 through any combination of common wired connections 252 and individual wired connections 254.

In the exemplary embodiment depicted in FIG. 2A, the adapter 240 also connects to the device interface 242, through one or more wired connections 256. The wired connection 256 between the adapter 240 and the device interface 242 can be a single shared wired connection that communicates data to and from every medical device 250 connected to the adapter 240. The adapter 240 can also communicate with the device interface 242 through a plurality of wired connections 256, wherein each wired connection 256 is dedicated to communicating with a separate medical device 250. The adapter 240 can also communicate with the device interface 242 through any combination of dedicated or shared connections.

The adapter module 310 may be removably attached to the rest of the case 300 to allow different modules with different types of wired connection ports to be interchangeably used, as depicted in FIG. 2B. The adapter module 310 may include any of the elements of the medical data interchange device 200, as well as any other desired systems and devices.

Figure 3C:
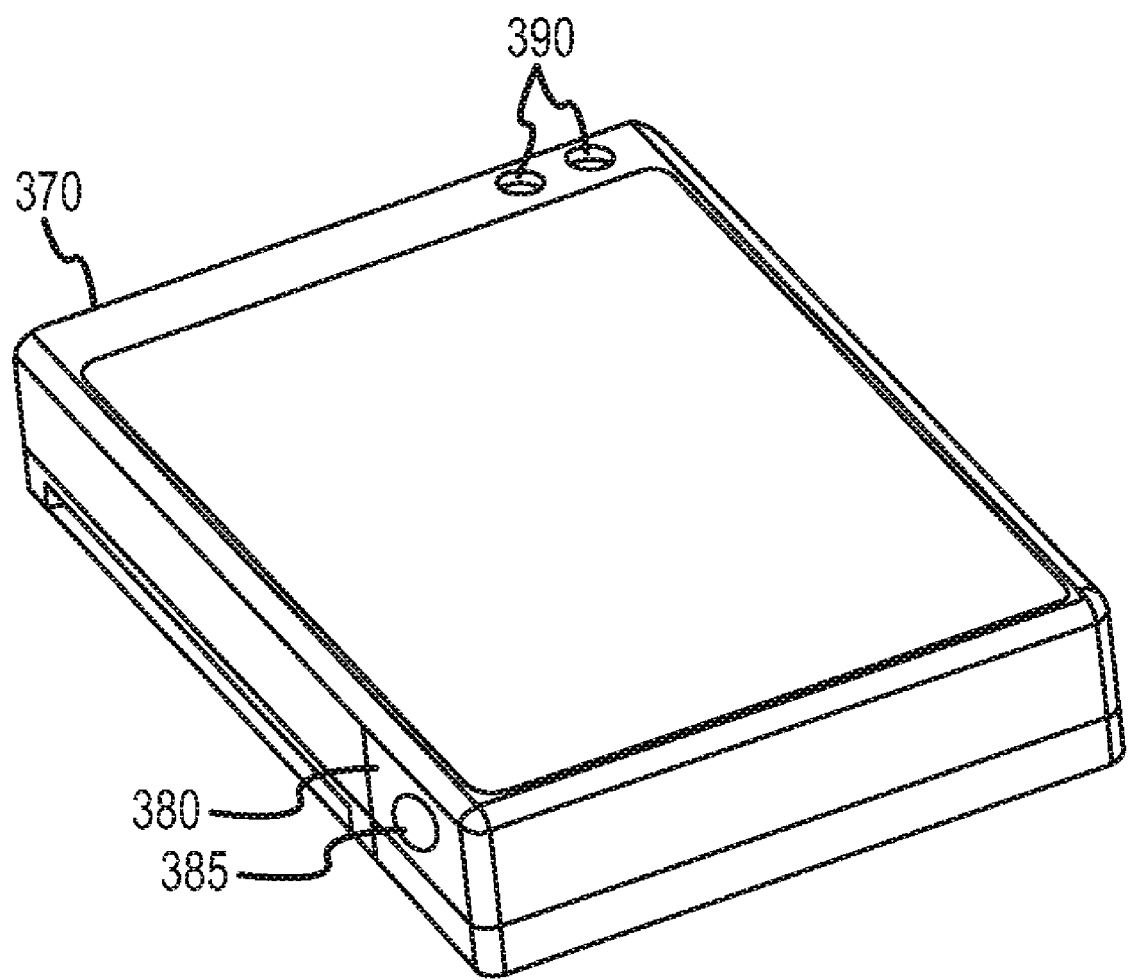
FIGS. 3C and 3D depict perspective views of another embodiment of an external casing for a medical data interchange device according to various aspects of the present invention.
Figure 3D:
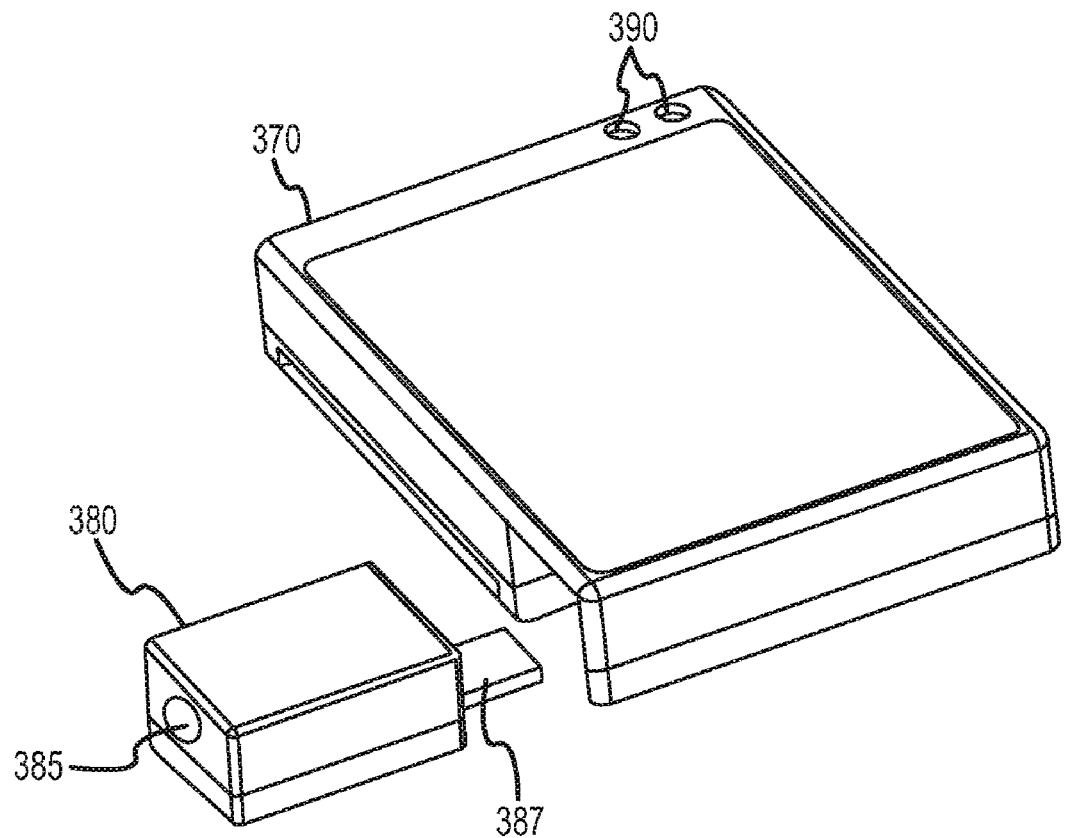
Figure 3E:
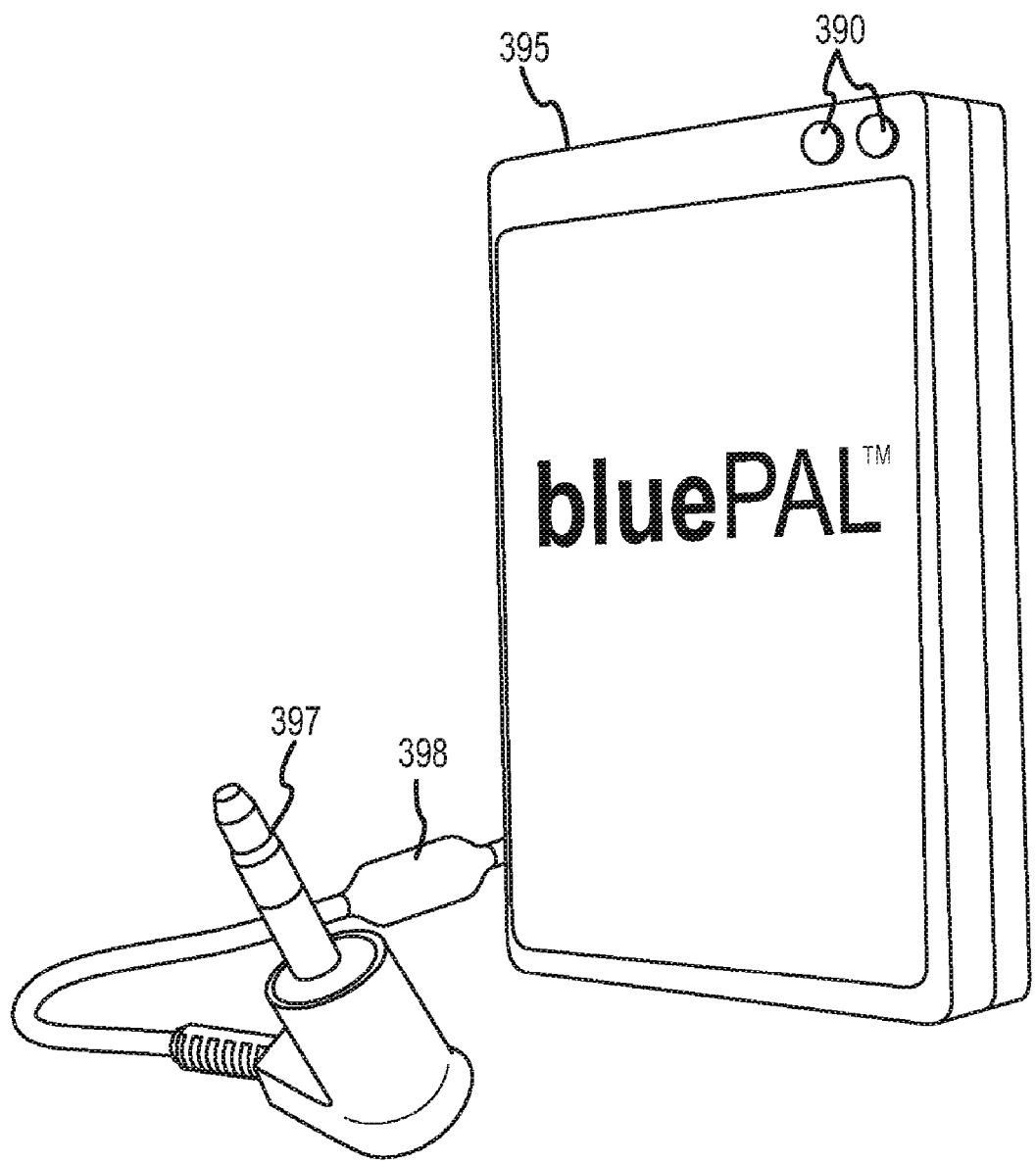
FIG. 3E depicts a perspective view of yet another embodiment of an external casing for a medical data interchange device according to various aspects of the present invention.

In another exemplary embodiment of the present invention, referring now to FIGS. 3C and 3D, a case 370 includes a removable adapter module 380 that includes a medical device connector 385 for communicating with a medical device through a wired connection. The adapter module 380 connects to the case 370 using plug 387. The plug 387 attaches to a corresponding port on the case 370 (not shown) to hold the adapter module 380 in place and allow the communication of data through the adapter module 380. The connector 385 and plug 387 can use any desired wired connection, and need not use the same type of wired connection. In one embodiment, for example, referring to FIG. 3E, a case 395 includes a 2.5 mm or 3.5 mm stereo plug connector 397 connected to a USB jack on the side of the case 395 (not shown). In this embodiment, the adapter module 380 is implemented in a component 398 that electrically couples the stereo plug connector 397 and USB jack. The component 398 includes circuitry (such as that depicted in FIGS. 6 and 7) to convert and/or redirect the signals from the stereo plug 397 to the USB jack and vice versa.

The adapter module 380 connects to the case 370 using plug 387. The plug 387 attaches to a corresponding port on the case 370 (not shown) to hold the adapter module 380 in place and allow the communication of data through the adapter module 380. The connector 385 and plug 387 can use any desired wired connection, and need not use the same type of wired connection. In the present embodiment, for example, the connector 385 is a 2.5 mm or 3.5 mm stereo jack while plug 387 is a USB plug.

The case can include any other suitable features. For example, the case may include a screen, lights, LEDs, keys, and speaker and microphone grilles to support features of a user interface included in a system for medical data interchange. The exemplary systems for medical data interchange shown in FIGS. 2A, 2B, 3A, 3B, 3C, 3D, and 3E are all configured to fit in a container along with the medical device it communicates with to allow a user to easily transport the medical device and the data interchange device together. In the exemplary system for medical data interchange depicted in FIG. 2C, the medical data interchange device 200 is integrated within the case or packaging of the medical device 250 itself.

Other embodiments of systems for medical data interchange according to aspects of the present invention can be configured to be in small enough to be coupled with or integrated into a medical device 250 or an intermediary device 260. For example, a medical device 250 may be manufactured to include a medical data interchange device 200 within the packaging or housing of the medical device 250. Similarly, a medical data interchange device 200 can be integrated as part of an intermediary device 260 such as a cellular phone, PDA, or other mobile computing device. The intermediary device 260 could thus be configured to both receive data from a medical device 250 through a wired connection, as well as transmit messages regarding the medical device 250 and/or patient to a medical data server 270.

Alternatively, a medical data interchange device 200 can be configured to be physically attached to a medical device 250 or intermediary device 260. For example, where an intermediary device 260 such as a mobile wireless telephone or PDA is used in conjunction with embodiments of the present invention, one exemplary embodiment of a medical data interchange device 200 and its case 300 is configured to match the size and shape of the of the intermediary device 260 and attach to the back of the intermediary device 260 using metal or plastic clips that wrap around the face and/or sides of the intermediary device 260. When attached, the medical data interchange device 200 conforms to the size and shape of the outline of the intermediary device 260, and is preferably shaped to conform to the dimensions of the back of the intermediary device 260 to avoid unnecessarily impacting the original size of the intermediary device 260. In this embodiment, the case of the medical data interchange device 200 may also include other desirable features, such as a belt clip to allow the data interchange device/intermediary device combination to be worn by a user.

Figure 4:
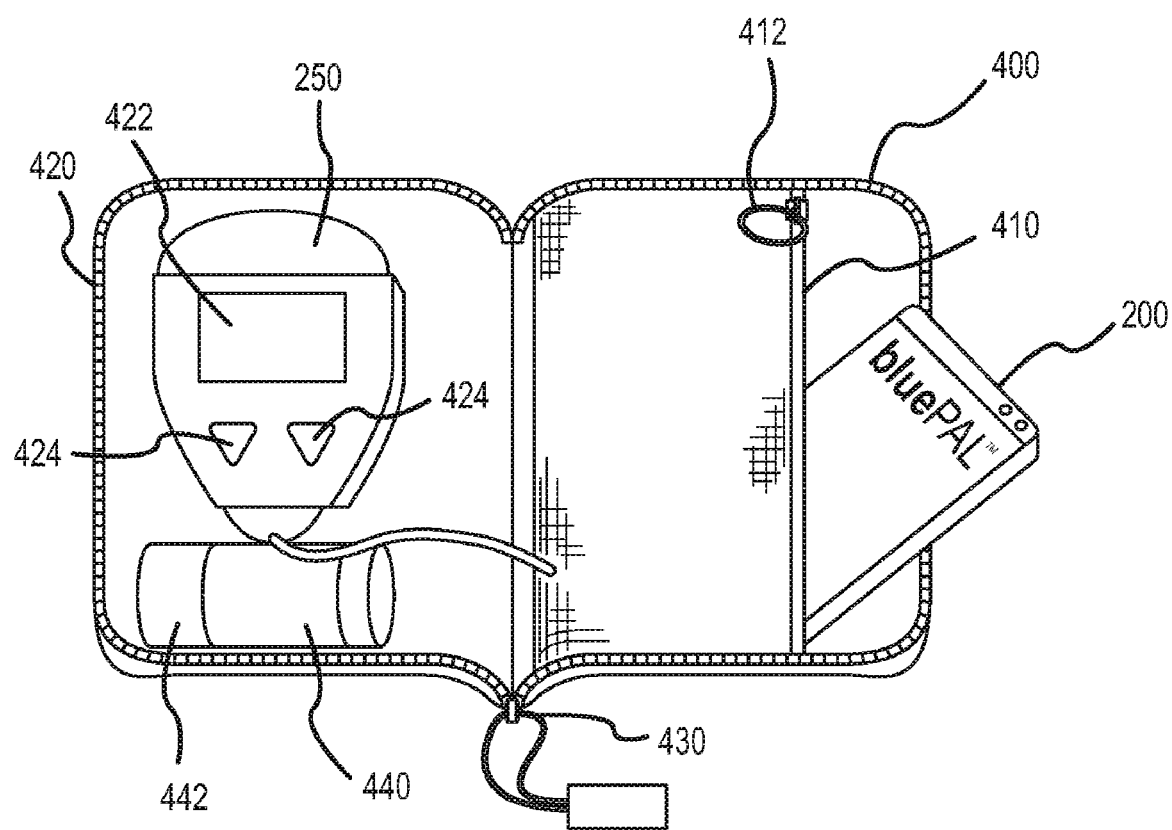
FIG. 4 depicts the interior of an exemplary container for holding a medical device and medical data interchange device according to various aspects of the present invention.

Turning to FIG. 4, in another exemplary embodiment of the present invention, the medical data interchange device 200 is contained in a flexible, protective container 400 that opens to allow a medical device 250 to be likewise contained therein. The container 400 could also be configured to hold an intermediary device 260 (such as a cellular phone, PDA, or other mobile computing device) to allow a medical data interchange device 200 to be used with a variety of intermediary devices 260, which may (in some cases) provide a more cost effective approach to integrate the medical data interchange device 200 with an intermediary device 260 or medical device 250. The medical data interchange device 200 can also be integrated within the protective container 400 itself, with the container 400 acting as the case for the data interchange device 200.

Alternatively, as depicted in FIG. 4, the medical data interchange device 200 may simply be contained within a pouch 410 or other structure within the container 400. The exemplary container 400 depicted in FIG. 4 also includes a holder 420 for the medical device 250 formed from clear plastic to allow a user to read a display 422 and/or operate keys 424 on the medical device 250. The protective container 400 can also be sized to comfortably fit and protect any other desired item, such as a day planner, wallet, notepad, and/or writing utensil or PDA stylus. The protective container 400 can be made from any combination of desired materials, such as leather, plastic, nylon, cordura, or other flexible material. The protective container 400 can be sealed in any manner, such as by using snaps, hook-and-loop closures, buttons, and/or a zipper. The exemplary container 400 depicted in FIG. 4, for example, is sealed using a zipper 430. The container 400 can be waterproof, heat resistant, and/or include padding to protect the medical data interchange device and other contents from the shock of a fall. The container 400 may include any number of pockets, pouches, or other sub-containers inside or outside the case to hold accessories associated with the medical device 250, intermediary device 260, or other item(s) stored within the container 400.

The exemplary protective container 400 depicted in FIG. 4 is configured to hold a medical device 250 (specifically, a glucose meter) and a medical data interchange device 200 according to an aspect of the present invention. In this exemplary embodiment, the protective container 400 is closed using a zipper 430 that runs along the exterior of the sides of the container 400. A user unzips the two halves of the container 400 and opens the container 400 to display the glucose meter contained in the holder 420 attached to the interior of one half of the container 400, while the medical data interchange device 200 is contained in a pouch 410 attached to the interior of the other half of the container 400. The pouch 410 is formed from a nylon mesh material to allow a user to see and/or interact with user interface features of the medical data interchange device 200. The pouch 410 is sealed with a zipper 412. The container 400 includes a flexible elastic strap 440 to hold a container of blood sugar metering strips 442. The container 400 may include any number of other pouches or containers on the interior or exterior of the container for storing batteries and/or power cables for the glucose meter and/or medical data interchange device, and other items of use to the patient carrying the container, such as bottles of insulin and needles for use by the patient depending on the outcome of a reading by the glucose meter.

Processor 210

Figure 5A:
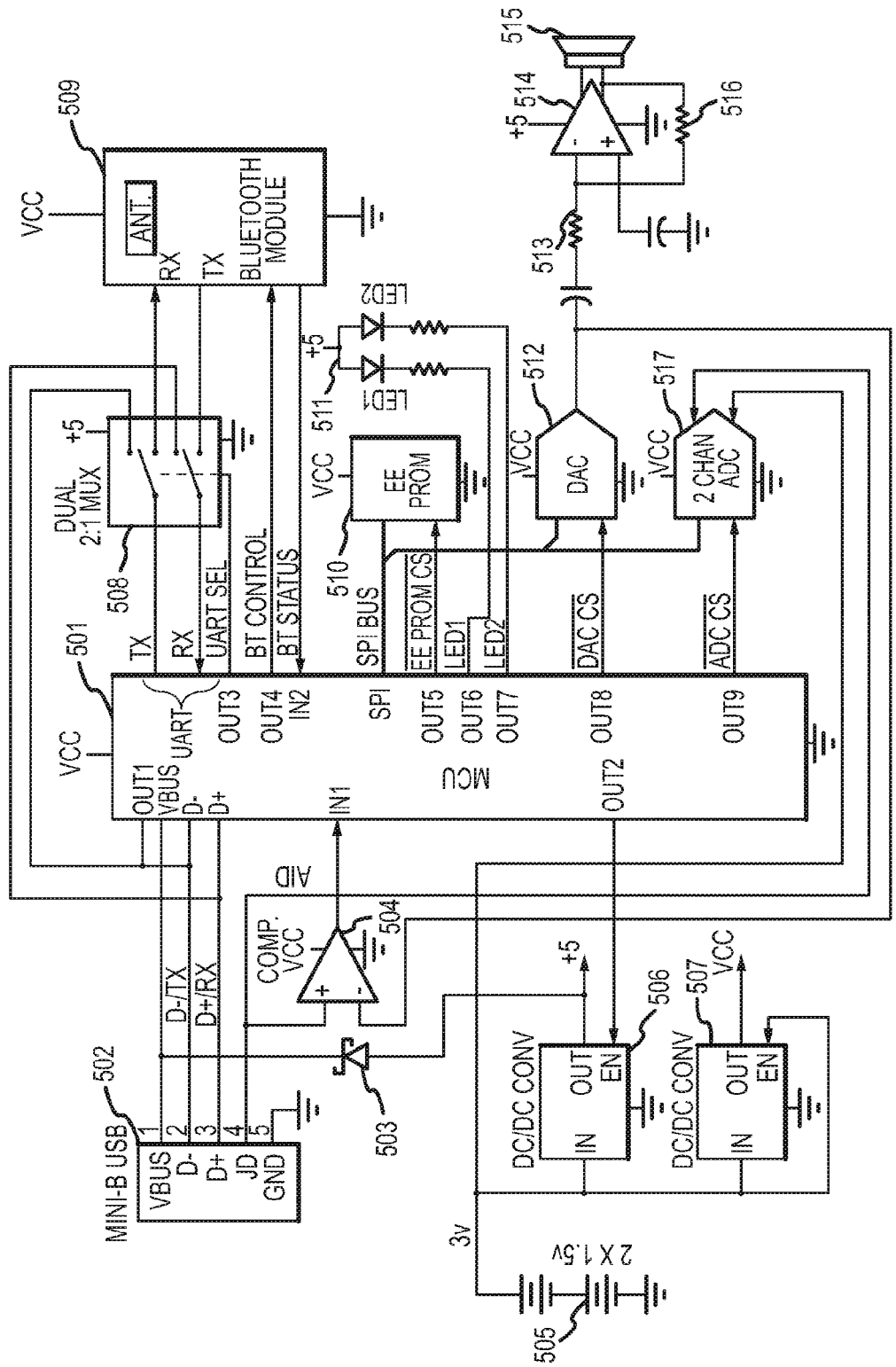
FIGS. 5A and 5B are a circuit diagrams depicting elements of an exemplary medical data interchange device according to various aspects of the present invention.

The processor 210 retrieves and executes instructions stored in the memory 220 to control the operation of the medical data interchange device 200. Any number and type of processor(s) such as an integrated circuit microprocessor, microcontroller, and/or digital signal processor (DSP), can be used in conjunction with the present invention. Referring now to FIG. 5A, an exemplary medical data interchange device 200 according to an aspect of the present invention is implemented using a microcontroller 501. In the exemplary system depicted in FIG. 5A, the microcontroller 501 includes a Universal Asynchronous Receiver/Transmitter (UART) and Universal Serial Bus (USB). The microcontroller 520 depicted in FIG. 5B also includes these features, along with a digital signal processor (DSP) for communication with a cellular RF Transceiver 530 as will be discussed in more detail below. The microcontrollers 501, 520 depicted in FIGS. 5A and 5B, respectively can include any other suitable components and features, such as comparators (504), analog-to-digital converters (ADCs) (517), and/or digital-to-analog converters (DACs) (512), though these components have been shown outside the microcontrollers 501, 520 for clarity.

Memory 220

The exemplary systems depicted in FIGS. 2A and 2B include a memory 220. The memory 220 stores instructions, medical device data, messages transmitted to or received from the medical data server 270, and any other suitable information. A memory 220 operating in conjunction with the present invention may include any combination of different memory storage devices, such as hard drives, random access memory (RAM), read only memory (ROM), FLASH memory, or any other type of volatile and/or nonvolatile memory.

Figure 5B:
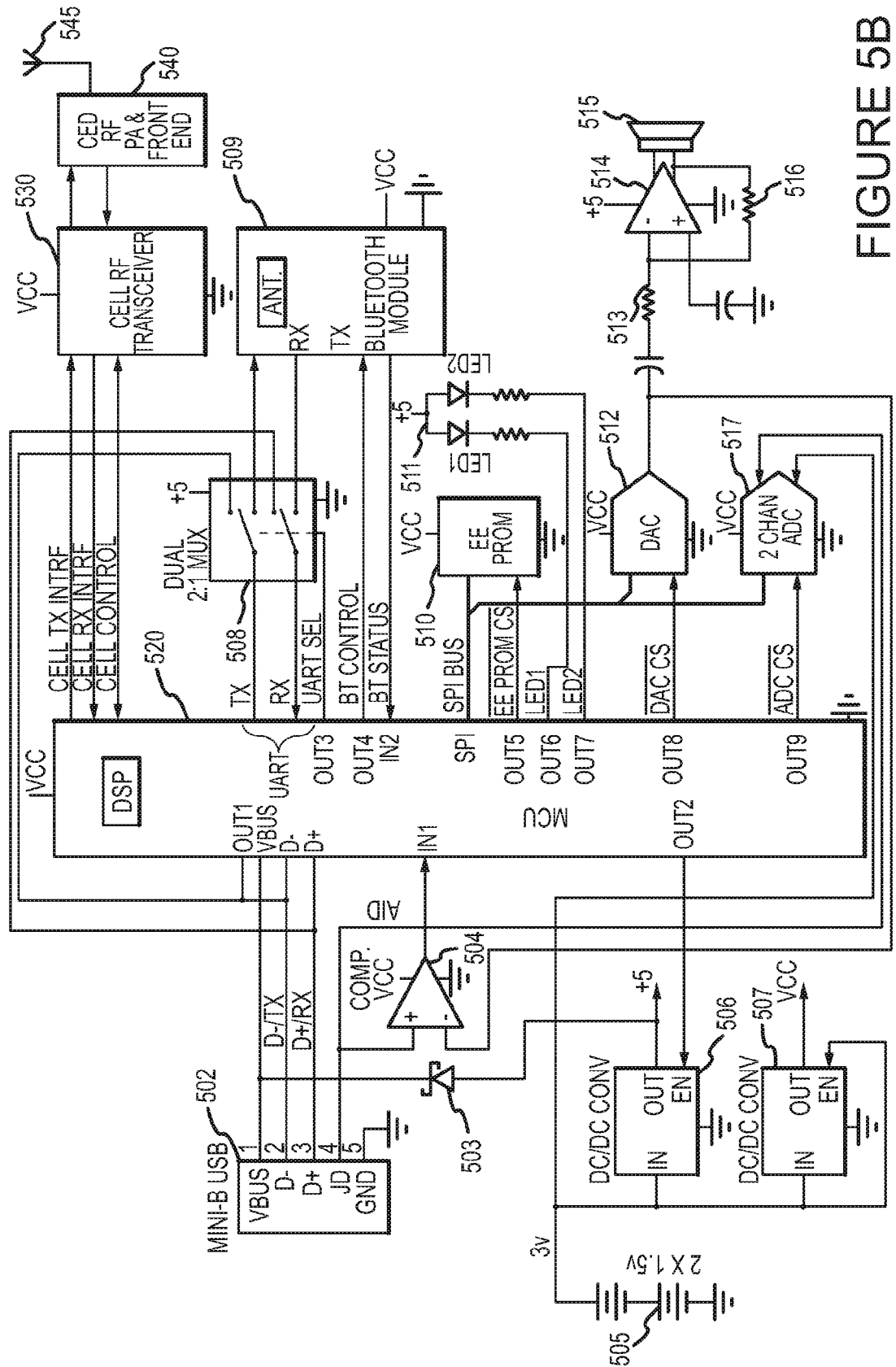

In the exemplary embodiments depicted in FIGS. 5A and 5B, the microcontroller 501 and 520 each include an on-chip memory. In addition, the microcontroller 501, 520 is coupled to a flash memory 510. The flash memory 510 may be of any size to achieve any desired purpose. In this exemplary embodiment, the size of flash memory 510 is selected to adequately store pre-recorded voice recordings to be played through the speaker 515, discussed below. Any number of memory storage devices of any size and configuration may also be used in conjunction with the present invention.

Power Source

Any number, combination, and type of suitable power sources can be utilized in accordance with aspects of the present invention. The exemplary systems depicted in FIGS. 5A and 5B are powered by a pair of replaceable alkaline AAA 1.5 volt batteries 505. The positive lead of the series-coupled battery pair 505 is connected to ADC 517 to enable the microcontroller 501, 520 to monitor the voltage level of the batteries 505. Any number of other suitable batteries may also be used according to any desired criteria. For example, a rechargeable battery or batteries integrated with the data interchange device may be selected to reduce the overall size of the medical data interchange device 200 and/or provide for the convenience of a user who would not need to replace batteries. Such rechargeable batteries can be charged through the USB connector 502, as well as through a dedicated power connector. Any battery of any suitable type and size may be used. Replaceable batteries may be selected to reduce the price of the medical data interchange device. The power supply circuitry shown in FIGS. 5A and 5B is exemplary only, and may be implemented by using other conventional power supply approaches. The medical data interchange device 200 and other systems for medical data interchange according to various aspects of the present invention can utilize any appropriate power supply devices, components, circuits, and systems.

In the exemplary circuits shown in FIGS. 5A and 5B, voltage from the batteries 505 is supplied to two DC to DC converters 506, 507 which supply an appropriate voltage level to the various components of the medical data interchange device 200. DC converter 506 steps up the voltage to 5 volts, while DC converter 507 steps up the voltage to 3.3 volts. Any number of voltage converters or similar components may be used as desired to supply appropriate voltage levels to components of the medical data interchange device 200.

Data Relay Transceiver 230

The data relay transceiver 230 communicates with one or more intermediary devices 260, medical data servers 270, or other suitable systems. Any suitable communications device, component, system, and method may be used in conjunction with the present invention. In the exemplary circuits shown in FIGS. 5A and 5B, the data relay transceiver 230 comprises a Bluetooth transceiver 509 that is in bidirectional communication with microcontroller 501, 520 through multiplexer 508. The multiplexer 508 allows the microcontroller 501, 520 to alternately communicate with the USB port 502 and the Bluetooth transceiver 509 through a single UART on the microcontroller 501, 520.

The medical data interchange device 200 may include, or operate in conjunction with, any number of data relay transceivers 230. In FIG. 5B, for example the exemplary medical data interchange device 200 further includes a cellular radio frequency (RF) transceiver 530 in communication with microcontroller 520. In this exemplary embodiment, the microcontroller 520 is a cellular baseband processor that includes a digital signal processor (DSP) which communicates data through a cellular RF power amplifier and front end 540 connected to a cellular antenna 545. Data is transmitted by the microcontroller 520 on the CELL TX INTRF line and received by the microcontroller on the CELL RX INTRF line. Additionally, the microcontroller 520 can control various features of the RF transceiver 530 via the CELL CONTROL line. The RF power amplifier and front end 540 performs the necessary functions to transmit and receive cellular signals, such as power amplification, power detection, filtering, and input/output matching.

The medical data interchange device 200 depicted in FIG. 5B may be configured to communicate using any number and type of cellular protocols, such as General Packet Radio Service (GPRS), Global System for Mobile Communications (GSM), Enhanced Data rates for GSM Evolution (EDGE), Personal Communication Service (PCS), Advanced Mobile Phone System (AMPS), Code Division Multiple Access (CDMA), Wideband CDMA (W-CDMA), Time Division-Synchronous CDMA (TD-SCDMA), Universal Mobile Telecommunications System (UMTS), and/or Time Division Multiple Access (TDMA). A medical data interchange device 200 operating in conjunction with the present invention may alternatively (or additionally) include data relay transceiver 230 components to communicate using any other method of wired or wireless communication.

As discussed previously, the medical data interchange device 200 can transmit any data to any entity operating in conjunction with the present invention. For example, the medical data interchange devices 200 depicted in FIGS. 5A and 5B may transmit medical data to one or more intermediary devices 260, as well as to one or more medical data servers 270.

Adapter Module 240

Referring again to FIG. 2A, the exemplary medical data interchange device 200 includes an adapter module 240 for communicating with one or more medical devices 250 as well as other suitable systems. The adapter module 240 can be configured to communicate with any suitable class, type, and/or manufacturer of medical device 250. The adapter module 240 depicted in FIG. 2A is an external component that communicates with a device interface 242 in the medical data interchange device 200. In the exemplary circuits depicted in FIGS. 5A and 5B, the USB port 502 is configured to interface with a standard USB connection, as well as with the adapter interfaces 601 and 701 (shown on FIGS. 6 and 7, respectively) which utilize USB connectors, but not the USB communications protocol. Instead, the adapters depicted in FIGS. 6 and 7 implement a customized protocol tailored to communicating with medical devices 250 through ring/tip connectors 605 and 705. The microcontroller 501, 520 is configured to detect and utilize the same communications protocol as an adapter module 240 connected to port 502.

In accordance with various aspects of the present invention, the adapter module 240 can also be modular and removably attached to the body of the data interchange device 200, integrated as part of the data interchange device 200, or a combination of the two. In the exemplary embodiment of the present invention depicted in FIG. 2B, an adapter module 240 is removably attached to the body of the medical data interchange device 200 and includes the device interface 242 to allow different medical devices 250 to interoperate with the data interchange device 200. As new medical devices 250 and/or new wired connections are utilized, a modular adapter module 240 configured to communicate with the new device or new frequency can be added to the existing system.

Software running on or operating in conjunction with the adapter module 240 can be configured/updated through the device interface 242, auxiliary communication system 244, the user interface 290, or in response to a communication from an intermediary device 260 or medical data server 270 received through the data relay transceiver 230. This allows the functionality of the medical data interchange device 200 to be dynamically updated and avoids the expense of having to create custom hardware implementations for every type of medical device to be monitored.

Figure 6:
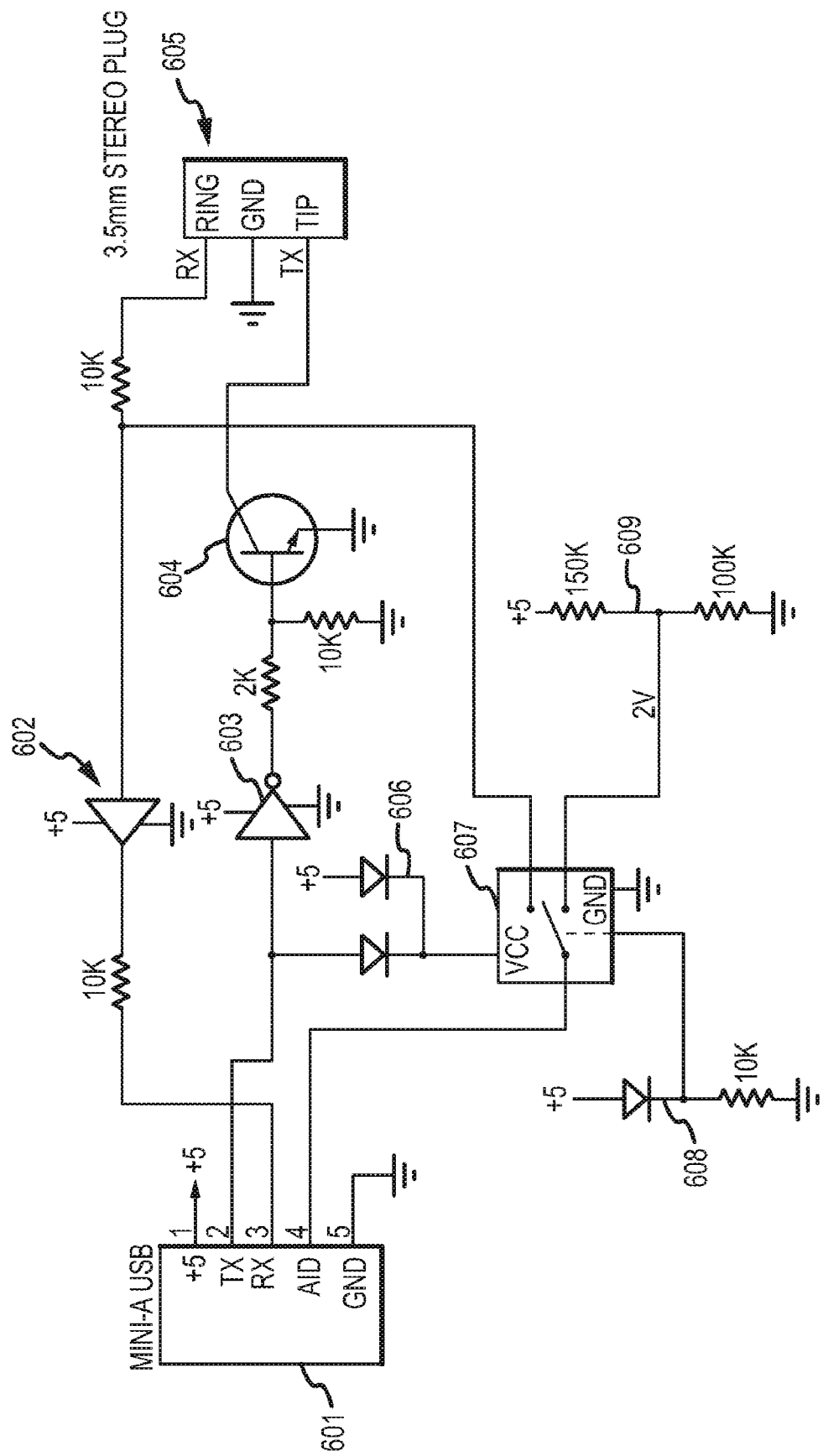
FIG. 6 is a circuit diagram illustrating elements of an exemplary embodiment of a smart cable with ID and wakeup capability.

FIG. 6 depicts a circuit diagram of an adapter module 240 that interfaces with the data interchange device 200 through a USB connector 601. As stated previously, the adapter 240 adjusts the voltage levels of Tx and Rx in order to communicate with a medical device 250 connected to TRS connector 605. An adapter 240 operating in conjunction with the present invention may use any combination of wired connections and communication protocols.

The adapter module 240 depicted in FIG. 6 is configured to interface with a medical device 250 that sends a wakeup signal. In operation, a signal received from the medical device 250 on the Rx line is provided to the USB connector 601 through a buffer 602 that provides isolation between the medical device 250 and the circuitry of the medical data interchange device 200 depicted in FIGS. 5A and 5B. The Rx signal is also provided to switch 607 which places a voltage on the AID pin of the USB connector 601. Referring back to FIGS. 5A and 5B, the voltage from the AID pin on connector 601 is provided to the comparator 504 through the ID pin on the USB port 502. The comparator 504 then activates the microcontroller 501, 520 in response. The level of voltage provided on the AID pin can also be used to identify the type of meter and/or adapter connected to the medical data interchange device 200 to the microcontroller 501, 520.

Referring again to FIG. 6, the Tx lead from the USB connector 601 is driven logically high when the UART on the microcontroller 501 is idle. The Tx signal from the USB connector 601 is inverted by inverter 603. When the UART on the microcontroller is idle, the inverter 603 drives the signal low, turning transistor 604 off and allowing the Tx signal to the tip of connector 605 to float at the voltage level from the medical device 250. Alternatively, when the UART on the microcontroller 501 is active, the Tx signal from the USB connector 601 is logically low and the inverter 603 inverts the low signal high to activate transistor 604 and allow the Tx signal from connector 601 to drive the Tx line on the TRS connector 605 to the medical device 250.

Figure 7:
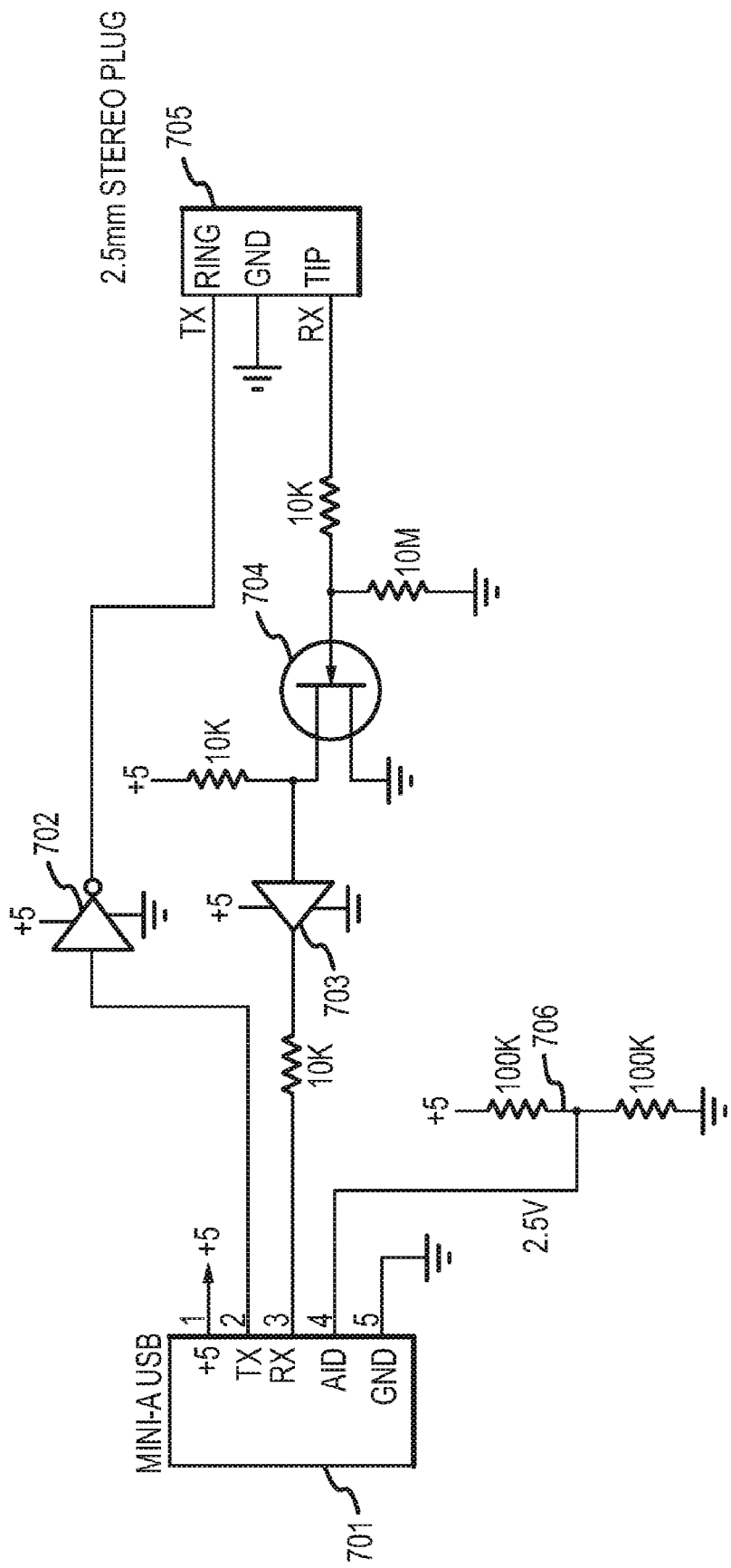
FIG. 7 is a circuit diagram illustrating elements of an alternate exemplary embodiment of a smart cable with ID capability.

FIG. 7 depicts a circuit diagram for another adapter 240 according to various aspects of the present invention. In this exemplary embodiment, USB connector 701 interfaces with USB port 502 shown in FIGS. 5A and 5B. Inverter 702 inverts the logic level of the Tx signal provided by the microcontroller 501 through the USB connector 701 to correspond to the voltage levels used by a medical device 250 connected to TRS connector 705. The Rx signal from a medical device 250 connected to the TRS connector 705 is provided to an N-channel JFET 704. In this exemplary circuit, when the Rx signal from the medical device 250 is marking (a −5.5 volt signal indicative of a logical "1") the JFET 704 is turned off, causing a 5-volt signal to be provided through buffer 703 and to the Rx lead of the UART on the microcontroller 501. Alternatively, when the Rx signal from the medical device 250 is spacing (a 6-volt signal indicative of a logical "0") the JFET 704 is turned on, causing ground to be provided through buffer 703 and to the Rx lead of the UART on the microcontroller 501, 520. The present invention can be configured to operate in conjunction with any other combination of voltages between the microcontroller 501, 520 and the TRS connector 705.

Device Interface 242

The device interface 242 communicates with one or more medical devices 250. The device interface 242 can also communicate with any other system, device or entity. The device interface 242 may include any number and combination of hardware and/or software components. The device interface 242 can communicate with medical devices through an adapter 240, as shown in FIG. 2A. In this exemplary embodiment, the device interface 242 connects to an external adapter 240 configured to couple with one or more medical devices 250. In this way, adapters 240 that allow connections to different medical devices can be used interchangeably with the same medical data interchange device 200. In another exemplary embodiment, referring to FIG. 2B, the device interface 242 is integrated with the adapter 240.

Any number of adapter modules 240 may be used in conjunction with the present invention, for example to communicate with multiple medical devices 250 using different wired connections and/or communication protocols. The present invention may be used in conjunction with any wired connection and communication protocol to communicate with one or more medical devices. For example, the medical data interchange device 200 may be configured to communicate with one or more medical devices using, without limitation: tip and sleeve (TS), tip, ring, and sleeve (TRS), and tip, ring, ring, and sleeve (TRRS) connections; serial peripheral interface bus (SPI) connections; universal serial bus (USB) connections; RS-232 serial connections, Ethernet connections, optical fiber connections, and Firewire connections.

In the exemplary embodiments depicted in FIGS. 2A and 2B, the device interface 242 and/or adapter 240 can be configured (e.g. through a software program residing in memory 220 and executed by processor 210) to detect and switch to different communication protocols and/or different wired connections to one or more medical devices 250 or other devices (such as the computer system 280), thus providing interoperability between types and manufacturers of a wide variety of devices. The auxiliary communication system 244 depicted in FIG. 2B may similarly be configured.

The medical data interchange device 200 can be configured to automatically request data from one or more medical devices 250 at predetermined times using the device interface 242. Any appropriate date or time setting may be used. The data interchange device 200, medical device 250, or any other device operating in conjunction with the present invention can be configured to automatically request and/or transmit data in any suitable manner. For example, the medical data interchange devices 200 depicted in FIGS. 2A and 2B can be configured through the device interface 242, the user interface 290, and/or from a command issued transmitted by an intermediary device 260 through the data relay transceiver 230. Additionally the medical data interchange device depicted in FIG. 2B can be configured through the auxiliary communication system 244. In the case of a command received through the data relay transceiver 230, the command can be generated by any suitable entity, such as from a medical data server 260 or a user of the intermediary device.

The automatic requesting/transmission of data by a device operating in conjunction with the present invention may be subject to any suitable conditions or rules that dictate whether the data is in fact requested/transmitted. For example, a medical data interchange device 200 programmed to request data from a medical device 250 at a set time may first check to verify that the medical device is within range, that the translator 200 has sufficient battery reserves to send the request and receive the data, whether the translator 200 has sufficient space in the memory 220 to store the data, and/or whether any other suitable condition is met.

Auxiliary Communication System 244

The medical data interchange device 200 depicted in FIG. 2B includes an auxiliary communication system 244 for communicating with additional systems and devices. For example, the auxiliary communication system 244 may be used to communicate with an external personal computer system 280 to upload software to the data interchange device 200, store data, provide or update encryption keys, perform diagnostics, and other appropriate purposes. The auxiliary communication system 244 can be a separate device, system, and/or component, or may be integrated with another component, such as the device interface 242. For example, in one embodiment of the present invention, the device interface 242 includes a USB port for communicating with any device capable of communicating through a USB connection. This allows the medical data interchange device 200 to communicate instructions, software upgrades, medical data, and other information with computing devices, memory storage devices (such as portable USB memory drives), as well as medical devices. The same device interface 242 can thus be used to receive medical data from a medical device 250 as well as to download reports that include the medical data. In one embodiment, medical data received by the medical data interchange device 200 may be formatted by the processor 210 into a ubiquitous data format such as Portable Document Format (PDF), and subsequently transferred to an external device such as a computer system 280 through the auxiliary communication system 244.

The medical data interchange device 200 or other system operating in conjunction with the present invention can include any suitable circuit, component, device, and system for communicating with any other device. The auxiliary communication system 244 can be used to transfer data to and from the medical data interchange device 200, as well as for an external computer system 280 to configure or program software and hardware in the data interchange device 200. In one embodiment of the present invention, for example, a user operating computer system 280 connected to medical data interchange device 200 through the Internet can configure settings for the device interface 242, adapter 240, data relay transceiver 230, and user interface 290. The computer system 280 can also download user data received by the data interchange device 200 from one or more medical devices 250. Additionally, the computer system 280 may communicate with the medical devices 250 real-time through the medical device transceiver 240, such as to monitor or control one or more medical devices 250 in real-time.

User Interface 290

The medical device 250, medical data interchange device 200, intermediary device 260, or other device operating in conjunction with the present invention may include a user interface. Referring to FIGS. 2A and 2B, an exemplary user interface 290 of a medical data interchange device 200 in accordance with aspects of the present invention includes an input device 292 and an output device 294. The input device 292 receives commands, data, and other suitable input from a user. The output device 294 provides the user with data, alerts, and other suitable information from the medical data interchange device 200.

Any number of input devices may be included in a user interface for one or more devices in the present invention. In one embodiment of the present invention, for example, the user interface 290 includes a touch pad, a touch screen, or an alphanumeric keypad to allow a user to enter instructions and data into the medical data interchange device 200. One or more buttons on the keypad or touch screen can be programmed or configured to perform specific functions, such as to request data from one or more medical devices. The user interface 290 can also include one or more multifunction switches, keys, or buttons that each allows a user to perform multiple functions.

The user interface may also include a microphone to allow the user to provide such information to the medical data interchange device 200 verbally. In this exemplary embodiment, the medical data interchange device 200 also includes speech recognition software to process verbal input through the user interface 290. The ability of the medical data interchange device to recognize speech from a patient can be particularly useful for users/patients who have vision problems, arthritis, or other impairments that would inhibit them from using a keypad or other input device. A microphone can be used in conjunction with audible (e.g. through sound waves perceivable by the human ear) data provided through a speaker, as discussed below, to allow a user to interact with any device operating in conjunction with the present invention in a completely auditory manner. In one nonlimiting example, audible input could also be sensed and analyzed by the medical data interchange device 200 that a patient has uttered a command, such as the command to turn on. Bidirectional audible communication, in addition to aiding impaired patients, allows users to operate devices in the present invention in a hands-free manner which can increase the speed, ease, and efficiency in which a device (such as the medical data interchange device 200) can be utilized.

Devices operating in conjunction with the present invention may include any number of suitable output devices. Referring to the exemplary medical data interchange device circuits depicted in FIGS. 5A and 5B, a user interface 290 including two lights 511 (LED1 and LED2) may be used to indicate the status of the medical data interchange device 200 to the user, as well as other pertinent information. For example, a flashing LED can be used to indicate when data from a medical device is in the process of being transferred, while a solid LED can indicate the transfer of data is complete. The medical data interchange devices 200 depicted in FIGS. 5A and 5B also provide auditory output through speaker 515. The microcontroller 501, 520 retrieves audio samples, such as recorded speech, from the EEPROM 510 and provides output to DAC 512, which converts the digital signal from the microcontroller 501, 520 to an analog signal that can be output on the speaker 515. The analog signal is provided to an audio amplifier 514 that amplifies the signal. The gain of the amplifier 514 is set by the ratio of resistors 516 and 513.

Any other suitable user interface features may similarly be included in devices and systems operating in accordance with the present invention. In another exemplary embodiment, for example, the output device 294 includes a display screen to visually display information as well as a speaker (e.g. speaker 515 shown in FIGS. 5A and 5B) to provide auditory output. The output device 294 can include multiple transducers such as audio speakers or piezoelectric elements, amplifiers, and other appropriate devices and systems to provide the auditory output. The medical data interchange device 200 may be configured to provide words, phrases, tones, recorded music, or any other type of auditory output to a user.

Any type of information may be communicated through the user interface 290, such as the biological, biometric, or behavioral information for one or more patients. The user interface can provide/receive any other suitable information, such as environmental information and/or diagnostic data for a medical device, a battery charge level, a temperature, a barometric pressure, a code relating to an accessory for the medical device, a biometric access measurement, a data validity measurement, an elapsed time since a previous reading by the medical device, a test result parameter, a signal-to-noise parameter, and a quality of service (QoS), and combinations thereof.

Information provided or received by the user interface 290 may be in any appropriate format. For example, a user interface that communicates information to a user in an auditory format may first provide a data header followed by a data value to identify the data to the user. Similarly, an output device 294 providing information to a user visually may provide a series of measurements in the form of a spreadsheet with headers indicating the source of the measurements. The output device 294 can also provide information in any number of desired languages, regardless of whether the information is provided audibly or visually.

Various features of the user interface can be implemented in hardware, software, or a combination of the two. In the medical data interchange devices 200 depicted in FIGS. 2A and 2B, for example, the user interface 290 includes voice interface software stored in the memory 220, including tables of recorded words and phrases. When executed by the processor 210, the voice interface software plays the appropriate recorded words and phrases (such as enunciating the medical data) through a speaker such as one included in the output device 294 to provide information to the user. The voice interface software, like any software operating on the medical data interchange device 200, can be downloaded and configured through the auxiliary communication system 244 or device interface 242. As discussed previously, any software program on any device operating in accordance with the present invention can be programmed or configured through any other suitable interface. In the medical data interchange device 200, for example, the voice interface software could also be downloaded and configured through the data relay transceiver 230 in response from a command from a medical data server 270 and/or intermediary device 260, as well as from input from the user through the user interface 290. Accordingly, the voice interface software can be configured to include words and phrases in any number of different languages, and can be updated with new words and phrases as desired, such as to accommodate a new medical device 250 operating with the medical data interchange device 200. Nonverbal sounds, such as melodies and tones, can also be stored and used by the user interface 294 to provide alerts, indicators, and other information to the user.

The user interface can also provide/receive information to a user in a machine-readable format. In one exemplary embodiment of the present invention, for example, the user interface 290 of a medical data interchange device 200 includes a fixed or retractable USB port to communicate with a thumb drive, memory stick, portable hard drive, an external computer system, or other USB-compatible device. This allows doctors and other healthcare providers to directly access the medical data interchange device 200 directly, without having to retrieve the data from a medical data server. In this exemplary embodiment, the medical data interchange device 200 can be configured to send, receive, and process machine-readable data can in any standard format (such as a MS Word document, Adobe PDF file, ASCII text file, JPEG, or other standard format) as well as any proprietary format. Machine-readable data to or from the user interface may also be encrypted to protect the data from unintended recipients and/or improper use. In an alternate embodiment, a user must enter a passcode to enable use of the USB port, and optionally, after a period of time of non-use, the USB port is automatically disabled. Any other user interface feature may be utilized to allow a human or non-human user to interact with one or more devices operating in conjunction with the present invention.

Power Saving Features

A medical data interchange device, intermediary device, medical device, or other system operating in accordance with aspects of the present invention may include any other suitable features, components, and/or systems. For example, the data interchange device 200 or other device may be configured to preserve the life of its battery by shutting off or going into a low-power mode when it, and/or the medical device it monitors, experiences a predetermined period of non-use, or a change in a measured parameter such as indication that a case holding the translator 200 has been actuated to a closed position. Such devices can also be configured to become active in response to any suitable event, such as receiving a signal from a device (such as a sensor).

Figure 8:
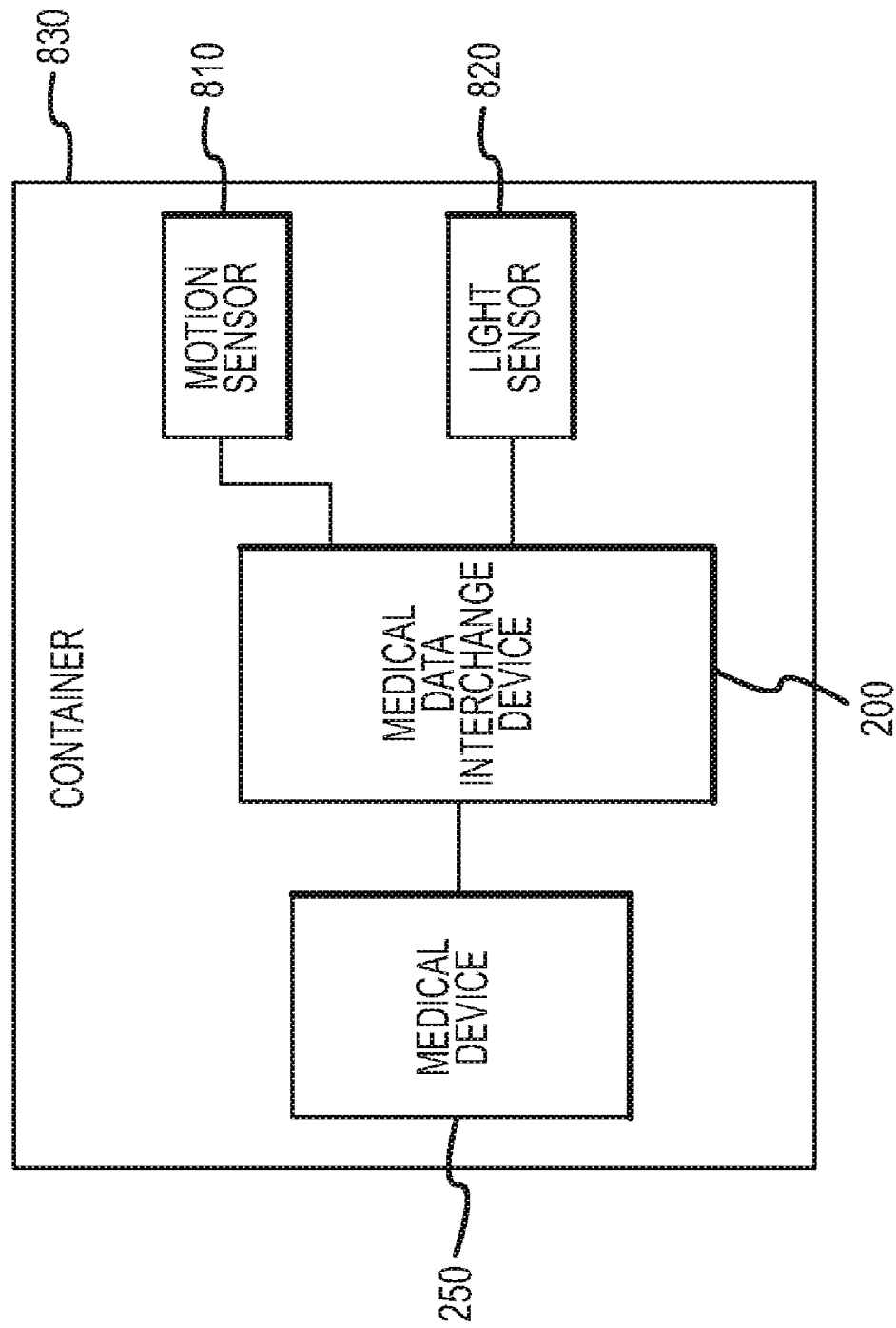
FIG. 8 is a block diagram depicting a container including light and motion sensors for activating a medical data interchange device in accordance with various aspects of the present invention.

In one non-limiting embodiment of the present invention, referring now to FIG. 8, a medical data interchange device 200 communicates with a motion sensor 810 and a light sensor 820 to determine when a container 830 holding the data interchange device 200 and the medical device 250 it monitors is open or closed. In this exemplary embodiment, the data interchange device 200 can preserve the life of its battery by shutting off or going into a low-power mode when the container 830 is closed and, therefore, the medical device 250 held in the container 830, is not in use. Any type of motion sensor can be used in accordance with the present invention, such as an accelerometer, tilt switch, or other device that generates a signal in response to movement. Similarly, any type of light sensor may be used in conjunction with the present invention. The light sensor can be used to detect the amount of light entering a container 830 holding the medical device, medical data interchange device, or other device to activate the device when the sensed amount of light exceeds a predetermined threshold, or if an increase in the amount of incident light exceeds a predetermined threshold. In an alternate embodiment, a microphone may receive audible signals that are analyzed by the medical data interchange device 200 to indicate a command has been uttered that indicates that the medical data interchange device 200 should be shut down or activated from a quiescent or low-power state.

A sensor may be integrated into the medical data interchange device 200, or operate externally to the data interchange device 200, communicating with the data interchange device 200 wirelessly or through a wired connection. For example, in the exemplary embodiment depicted in FIG. 8, the motion sensor 810 and light sensor 820 are integrated into the interior of the container 830 and communicate with a medical data interchange device 200 contained within to indicate when the container 830 is actuated from a closed position to an open position.

Security Measures

Systems and devices operating in accordance with aspects of the present invention may implement one or more security measures to protect data, restrict access, or provide any other desired security feature. For example, any device operating in conjunction with the present invention may encrypt transmitted data and/or protect data stored within the device itself. Such security measures may be implemented using hardware, software, or a combination thereof. Any method of data encryption or protection may be utilized in conjunction with the present invention, such as public/private keyed encryption systems, data scrambling methods, hardware and software firewalls, tamper-resistant or tamper-responsive memory storage devices or any other method or technique for protecting data. Similarly, passwords, biometrics, access cards or other hardware, or any other system, device, and/or method may be employed to restrict access to any device operating in conjunction with the present invention.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Methods illustrated in the various figures may include more, fewer, or other steps. Additionally, steps may be performed in any suitable order without departing from the scope of the invention. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiments without departing from the scope of the present invention. These and other changes or modifications are intended to be included within the scope of the present invention, as expressed in the following claims.

What is claimed is:

1. A medical data interchange device comprising:
a processor;
a plurality of device interfaces, wherein each device interface is configured to receive patient data directly from a plurality of different medical devices;
a data relay transceiver coupled to and communicating with at least one intermediary device, the data relay transceiver not capable of wireless communication with a medical device; and
a memory coupled to the processor and storing instructions that, when executed by the processor, cause the processor to:
transition from a quiescent state to an active state in response to a signal transmitted from a medical device to prepare the medical data interchange device to receive data from the medical device;

broadcast an authorization code stored in the medical data interchange device to the medical device in response to a request for authorization from the medical device for authenticating the medical data interchange device;

automatically detect, based on a voltage of the signal from the medical device, a communication protocol used by the medical device;

automatically configure a device interface of the plurality of medical device interfaces to communicate with the plurality of medical devices using the detected communication protocol;

receive data from the medical device through a wired connection using the configured device interface, wherein the data from the medical device is received by the medical data interchange device through an adapter coupled to the configured device interface, the adapter configured to communicate with the medical data interchange device using a first communication format and communicate with the medical device using a second communication format, the adapter being removably coupled to the medical data interchange device;

activate the intermediary device to transition from a quiescent state to an active state by transmitting a signal to prepare the intermediary device to receive the medical device data; and transmit the data to an intermediary device using the data relay transceiver.

2. The medical data interchange device of claim 1, wherein the data relay transceiver includes a wireless transmitter for transmitting the data wirelessly to the intermediary device.

3. The medical data interchange device of claim 1, further comprising a wired connecter in communication with the transceiver for transmitting the data to the intermediary device.

4. The medical data interchange device of claim 1, wherein the device interface comprises at least one of a:
- tip and sleeve (TS) connection;
- a tip, ring, and sleeve (TRS) connection;
- a tip, ring, ring, and sleeve (TRRS) connection;
- a serial peripheral interface bus (SPI) connection;
- a universal serial bus (USB) connection;
- an RS-232 serial connection;
- an Ethernet connection; and
- a FireWire connection.

5. The medical data interchange device of claim 1, wherein the device interface is configured to receive data from a plurality of different medical devices.

6. The medical data interchange device of claim 5, wherein the plurality of different medical devices include at least one of a blood glucose meter, a pacemaker, a blood pressure monitor, an insulin pump, a pulse oximeter, a holter monitor, an electrocardiograph, an electroencephalograph, a blood alcohol monitor, an alcohol breathalyzer, an alcohol ignition interlock, a respiration monitor, an accelerometer, a skin galvanometer, a thermometer, a patient geolocation device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) meter, an international normalized ratio (INR) meter, a tremor sensor, and a defibrillator.

7. The medical data interchange device of claim 1, wherein the device interface is configured to receive the data through a plurality of wired connections.

8. The medical data interchange device of claim 1, wherein the first communication format and the second communication format are the same communication format.

9. The medical data interchange device of claim 1, wherein the adapter is configured to communicate with the medical device through a plurality of wired connections.

10. The medical data interchange device of claim 1, wherein the adapter is configured to communicate with the medical data interchange device through a plurality of wired connections.

11. The medical data interchange device of claim 1, wherein the adapter is configured to receive data from a plurality of medical devices through a respective plurality of wired connections.

12. The medical data interchange device of claim 1, wherein the adapter is configured to receive data from a plurality of medical devices connected to a single transmission medium.

13. The medical data interchange device of claim 1, wherein the adapter is nonremovably coupled to the medical data interchange device.

14. The medical data interchange device of claim 1, wherein the adapter is removably coupled to the medical data interchange device.

15. The medical data interchange device of claim 1, wherein the adapter includes a first connector for attaching the adapter to the medical data interchange device and a second connector for attaching the adapter to the medical device.

16. The medical data interchange device of claim 15, wherein the first connector is removably attached to the adapter.

17. The medical data interchange device of claim 15, further comprising a first cable removably attached to the first connector and configured to couple the first connector to the medical data interchange device, and a second cable removably attached to the second connector and configured to couple the second connector to the medical device.

18. A medical data interchange device comprising:
a processor;
a plurality of device interfaces, wherein each device interface is configured to receive patient data directly from a plurality of different medical devices;
a data relay transceiver coupled to and communicating with at least one intermediary device, the data relay transceiver not capable of wireless communication with a medical device; and
a memory coupled to the processor and storing instructions that, when executed by the processor, cause the processor to:
transition from a quiescent state to an active state in response to a signal transmitted from a medical device to prepare the medical data interchange device to receive data from the medical device;
broadcast an authorization code stored in the medical data interchange device to the medical device in response to a request for authorization from the medical device for authenticating the medical data interchange device;
automatically detect, based on a voltage of the signal from the medical device, a communication protocol used by the medical device;

automatically configure a device interface of the plurality of medical device interfaces to communicate with the plurality of medical devices using the detected communication protocol;

receive data from a medical device through a wired connection using the configured device interface, wherein the data from the medical device is received by the medical data interchange device through an adapter coupled to the configured device interface, the adapter configured to communicate with the medical data interchange device using a first communication format and communicate with the medical device using a second communication format, the adapter being removably coupled to the medical data interchange device;

activate the intermediary device to transition from a quiescent state to an active state by transmitting a signal to prepare the intermediary device to receive the medical device data;

encrypt the data; and transmit the data to an intermediary device using the data relay transceiver.

19. The medical data interchange device of claim 18, wherein the device interface comprises at least one of a:

tip and sleeve (TS) connection;
a tip, ring, and sleeve (TRS) connection;
a tip, ring, ring, and sleeve (TRRS) connection;
a serial peripheral interface bus (SPI) connection;
a universal serial bus (USB) connection;
an RS-232 serial connection;
an Ethernet connection; and
a FireWire connection.

20. The medical data interchange device of claim 18, wherein the data is encrypted using at least one encryption key, the encryption key selected from the group comprising:

a private encryption key associated with the patient;
a private encryption key of a health care provider associated with the patient;
a public encryption key associated with at least one of:
an intended recipient, and
a medical data server; and
combinations thereof.

21. The medical data interchange device of claim 18, wherein the adapter is configured to communicate with the medical device through a plurality of wired connections.

22. The medical data interchange device of claim 18, wherein the adapter is configured to receive data from a plurality of medical devices through a respective plurality of wired connections.

23. The medical data interchange device of claim 18, wherein the adapter is configured to receive data from a plurality of medical devices connected to a single transmission medium.

24. The medical data interchange device of claim 18, wherein the adapter is removably coupled to the medical data interchange device.

25. The medical data interchange device of claim 18, wherein the adapter includes a first connector for attaching the adapter to the medical data interchange device and a second connector for attaching the adapter to the medical device.

* * * * *